United States Patent
Cheng et al.

(10) Patent No.: US 10,308,654 B2
(45) Date of Patent: Jun. 4, 2019

(54) PREPARATION AND USE OF KINASE INHIBITOR

(71) Applicant: CHANGZHOU LONGTHERA PHARMACEUTICALS INC, Changzhou (CN)

(72) Inventors: Peng Cheng, Changzhou (CN); Wenjie Cao, Changzhou (CN)

(73) Assignee: CHANGZHOU LONGTHERA PHARMACEUTICALS INC., Changzhou (CN)

( * ) Notice: Subject to any disclaimer, the term of this patent is extended or adjusted under 35 U.S.C. 154(b) by 0 days.

(21) Appl. No.: 15/566,872

(22) PCT Filed: Apr. 15, 2016

(86) PCT No.: PCT/CN2016/079495
§ 371 (c)(1),
(2) Date: Oct. 16, 2017

(87) PCT Pub. No.: WO2016/165657
PCT Pub. Date: Oct. 20, 2016

(65) Prior Publication Data
US 2018/0127419 A1  May 10, 2018
US 2018/0346467 A9  Dec. 6, 2018

(30) Foreign Application Priority Data

Apr. 17, 2015 (CN) .......................... 2015 1 0186101

(51) Int. Cl.
| | |
|---|---|
| *C07D 487/04* | (2006.01) |
| *A61K 31/52* | (2006.01) |
| *A61K 31/5377* | (2006.01) |
| *C07D 401/12* | (2006.01) |
| *C07D 473/28* | (2006.01) |
| *C07D 473/32* | (2006.01) |
| *C07D 473/36* | (2006.01) |
| *A61P 35/02* | (2006.01) |

(52) U.S. Cl.
CPC .......... *C07D 487/04* (2013.01); *A61K 31/52* (2013.01); *A61K 31/5377* (2013.01); *A61P 35/02* (2018.01); *C07D 401/12* (2013.01); *C07D 473/28* (2013.01); *C07D 473/32* (2013.01); *C07D 473/36* (2013.01)

(58) Field of Classification Search
CPC .............................. C07D 487/04; A61K 31/52
USPC ............................................................. 544/2
See application file for complete search history.

(56) References Cited

FOREIGN PATENT DOCUMENTS

| | | |
|---|---|---|
| CN | 103864792 A | 6/2014 |
| JP | 2006-516561 A | 7/2006 |
| JP | 2014-129361 A | 7/2014 |
| WO | WO 2004/065378 A1 | 8/2004 |
| WO | WO 2011/147066 A1 | 12/2011 |
| WO | WO 2015/006754 A2 | 1/2015 |

OTHER PUBLICATIONS

PCT/CN2016/079495, Jul. 4, 2016, International Search Report and Written Opinion.

*Primary Examiner* — Kahsay Habte
(74) *Attorney, Agent, or Firm* — Wolf, Greenfield & Sacks, P.C.

(57) ABSTRACT

Disclosed are a preparation method for a kinase inhibitor and a use thereof. The kinase inhibitor is a compound represented by formula (I) wherein the groups are defined as described in the description. The compound of formula (I) has a kinase inhibitory activity and therefore can be used for the preparation of medicines for treating kinase activity-related diseases.

13 Claims, No Drawings

PREPARATION AND USE OF KINASE INHIBITOR

RELATED APPLICATIONS

This application is a national stage filing under 35 U.S.C. § 371 of International Application PCT/CN2016/079495 entitled "PREPARATION AND USE OF KINASE INHIBITOR" filed Apr. 15, 2016, which claims priority to CN Application No. 201510186101.7, filed Apr. 17, 2015, the entire disclosure of each of which is incorporated by reference herein in its entirety.

TECHNICAL FIELD

The present invention relates to the field of medicinal chemistry. In particular, the present invention relates to the preparation and use of a novel kinase inhibitor.

BACKGROUND

Cell cycle abnormality is a hallmark of cancer. Cyclin-dependent kinase (CDK) is a class of serine/threonine kinases that play a central role in the cell cycle, leading the activation, progression and end of the cell cycle. The CDK family includes CDK1-13.

CDK4/6 is over-active in many cancers, leading to cell proliferation out of control. Studies find that the overexpression of CyclinD1 and CDK4 may be involved in the occurrence of esophageal cancer, and the increased expression of both is related to the degree of differentiation of esophageal cancer. CDK4 is generally expressed in both benign and malignant pancreatic endocrine tumors. The expression of CDK4 in lung cancer tissues is also significantly higher than that in normal lung tissues. The degree of high positive expression is positively correlated with histopathological classification of lung cancer, lymphatic metastasis and clinical stage malignancy, which is a potential poor prognostic factor. CDK6 is also overexpressed in a variety of tumor cells, for example, CDK6 is detected to be overexpressed in male hormone-sensitive prostate cancer cell lines. And the exogenous overexpression of CDK6 leads to accelerated growth of tumor cell, while the growth rate of tumor cells interfered with CDK6 is significantly slower.

CDK4 and CDK6 have 71% homology to the amino acid composition, and this result suggests their functional similarity. Recent studies also reveal that CDK4/6-CyclinD can phosphorylate the transcription factor FOXM1, improving its stability and activity in melanoma. Thus, inhibition of CDK4/6 can achieve cell proliferation inhibition from downstream of the signaling pathway. The combination of CDK4/6 inhibitors and endocrine therapy can achieve a double inhibitory effect, and the preclinical study also confirms that the combination of CDK4/6 inhibitors and endocrine therapy has a significant synergistic effect.

CDK family inhibitors have received widespread attention as a potential target for tumor therapy over the past 20 years. However, the first generation of CDK inhibitors lacks selectivity and is a pan-inhibitor, such as flavopiridol which can inhibit CDK1, CDK2, CDK4, CDK6, CDK7 and CDK9. Although flavopiridol can induce cell cycle arrest, and show the role of cytotoxicity, clinical efficacy is unsatisfactory. The second generation of CDK inhibitors is designed to improve selectivity, in particular, selective inhibitors targeting CDK4/6 alone which show better clinical efficacy and less toxic side effects receive significant attention. Pfizer's CDK4/6 dual inhibitor Palbociclib (trade name Ibrance) became the first listed CDK4/6 dual inhibitor, and FDA has approved it as a first-line drug for the treatment of ER-positive, HER2-negative breast cancer.

Novartis's LEE011 is a CDK4/CDK6 dual inhibitor, which is most sensitive to malignant rhabdoid tumor and neuroblastoma. LEE011 is mainly combined with aromatase inhibitors and PI3K inhibitors, and can play a better anti-tumor activity in clinical trials. LEE011 combined with letrozole is used for the treatment of metastatic HR positive/HER2 negative breast cancer in clinical stage III. LEE011 combined with BYL719 and letrozole is used for the treatment of metastatic HR positive breast cancer in clinical stage Ib/II.

In addition, Lilly's LY-2835219 is also in clinical stage III study. If these clinical trials can achieve the desired results, CDK4/CDK6 dual inhibitor will bring a large number of patients with advanced breast cancer more survival benefits.

As mentioned above, the development of CDK4/CDK6 selective dual inhibitor has become a frontier and focus area for anti-tumor drug research. Therefore, there is an urgent need to develop new CDK kinase inhibitors.

SUMMARY OF INVENTION

The object of the present invention is to provide a novel CDK kinase inhibitor, preparation method and use thereof.

In the first aspect of the present invention, a compound of formula I, or a pharmaceutically acceptable salt thereof is provided:

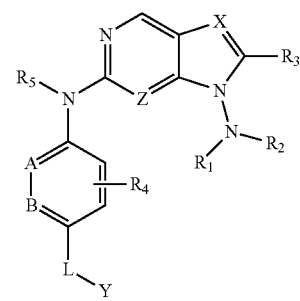

wherein, $R_1$ and $R_2$ are each independently selected from H, a substituted or unsubstituted C1-C8 alkyl, $C(O)OR_8$, $CONR_9R_{10}$, $C(O)R_{11}$, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

in addition, $R_1$ and $R_2$ can be connected with adjacent N atom to form a ring structure, said ring structure includes a substituted or unsubstituted 3-12 membered saturated or unsaturated heterocycle or a bridged ring or a spiro ring; wherein said heterocycle refers to a ring structure containing 0-3 heteroatoms selected from the group consisting of N, O or S, in addition to the nitrogen atom attached to the parent nucleus;

$R_3$ is selected from a substituted or unsubstituted C1-C8 alkyl, CN, $C(O)OR_{12}$, $CONR_{13}R_{14}$, $C(O)R_{15}$, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

R₄ is selected from H, a substituted or unsubstituted C1-C4 alkyl, a substituted or unsubstituted C1-C8 alkoxy, a halogen, OH, CN, C(O)OR₁₂, CONR₁₃R₁₄, C(O)R₁₅, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

R₅ is selected from H or C1-C4 alkyl;

X is CR₁₆ or N;

A, B, and Z are each independently selected from N or CR₁₆;

R₁₆ is H, C1-C4 alkyl or C1-C4 haloalkyl;

L is selected from the group consisting of none, C1-C6 alkylene, C(O), CONR₁₇ or S(O)₂;

Y is H, R₁₈, NR₁₉R₂₀, OH, or Y is selected from part of the group consisting of:

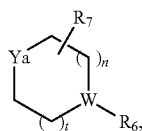

wherein,

R₆ is none, H, a substituted or unsubstituted C1-C8 alkyl, a substituted or unsubstituted C1-C8 alkoxy, a substituted or unsubstituted C2-C6 acyl, a substituted or unsubstituted C2-C6 sulfonyl, a substituted or unsubstituted C1-C6 alkylenehydroxy, CONR₂₂R₂₃ or C(O)R₂₄;

R₇ may be 0-3 substituents and R₇ is a substituted or unsubstituted C1-C8 alkyl, an oxygen or a halogen, or two or more R₇ form a bridged cycloalkyl; W is CR₂₁, N or O (when W is O, R₆ is absent);

Ya is CR₂₁ or N; R₂₁ is H or a halogen;

R₈, R₉, R₁₀, R₁₁, R₁₂, R₁₃, R₁₄, R₁₅, R₁₇, R₁₈, R₁₉, R₂₀, R₂₂, R₂₃ and R₂₄ are each independently selected from H, a substituted or unsubstituted C1-C8 alkyl, a substituted or unsubstituted C1-C8 alkoxy, a substituted or unsubstituted C1-C6 alkyleneamino, a substituted or unsubstituted C1-C6 alkylenehydroxy, a substituted or unsubstituted 5-8 membered aryl, a substituted or unsubstituted 5-8 membered heteroaryl, a substituted or unsubstituted 3-12 membered saturated heterocycle or carbocycle; wherein said heteroaryl contains at least one heteroatom selected from the group consisting of N, O or S, said heterocycle contains at least one heteroatom selected from the group consisting of N, O or S;

n and t are 0, 1 or 2, respectively;

any one of the above mentioned "substituted" means that one or more hydrogen atoms on the group are substituted with substituent(s) selected from the group consisting of a halogen, OH, NH₂, CN, an unsubstituted or halogenated C1-C8 alkyl, C1-C8 alkoxy, an unsubstituted or halogenated C2-C6 alkenyl, an unsubstituted or halogenated C2-C6 alkynyl, an unsubstituted or halogenated C2-C6 acyl, an unsubstituted or halogenated 5-8 membered aryl, an unsubstituted or halogenated 5-8 membered heteroaryl, an unsubstituted or halogenated 3-12 membered saturated heterocycle or carbocycle; wherein said heteroaryl contains 1-3 heteroatoms selected from the group consisting of N, O or S, said heterocycle contains 1-3 heteroatoms selected from the group consisting of N, O or S.

In another preferred embodiment,

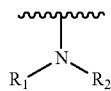

is a substituted or unsubstituted group selected from the group consisting of

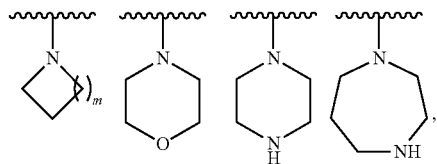

wherein m is 0, 1, 2, 3, 4, 5, 6, 7, 8 or 9, and said "substituted" is defined as described above.

In another preferred embodiment, R₁ and R₂, together with the adjacent nitrogen atom, form a 4-12 membered ring structure.

In another preferred embodiment, R₁ and R₂, together with the adjacent nitrogen atom, form a 5-7 membered ring structure.

In another preferred embodiment, R₁ and R₂, together with the adjacent nitrogen atom, form a 6 membered ring structure.

In another preferred embodiment, R₁₃ and R₁₄, together with the adjacent nitrogen atom, form a 4-6 membered ring structure.

In another preferred embodiment, when L is none, Y is a 6 membered heterocycle containing nitrogen atom.

In another preferred embodiment, A, B, L, X, Y, Z, R₁, R₂, R₃, R₄ or R₅ is the corresponding group in the specific compounds described in the examples.

In another preferred embodiment, the compound of formula I is a compound as shown below:

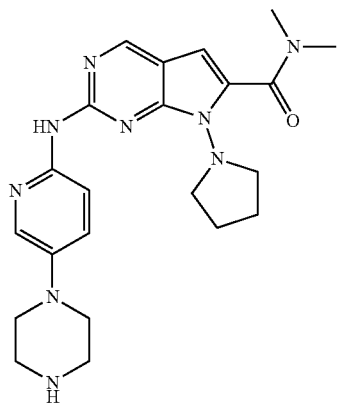

-continued
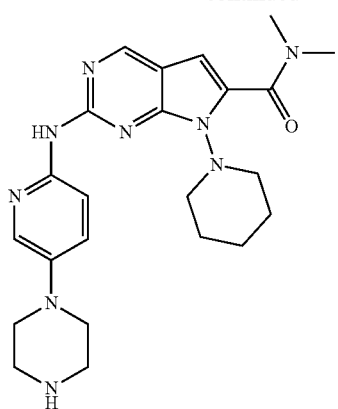
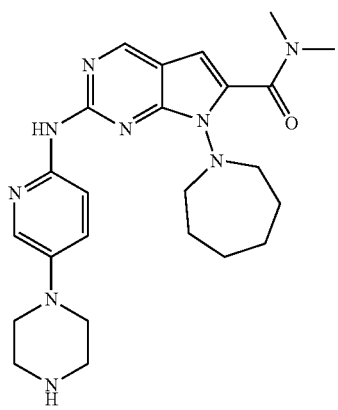
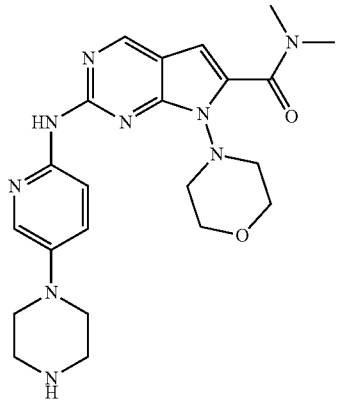
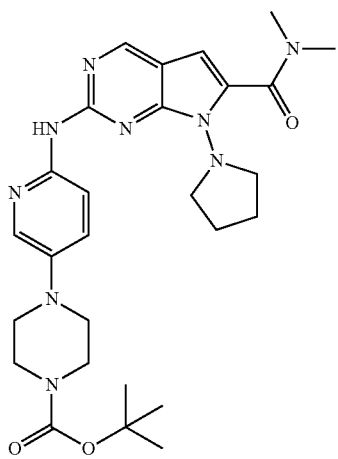
-continued
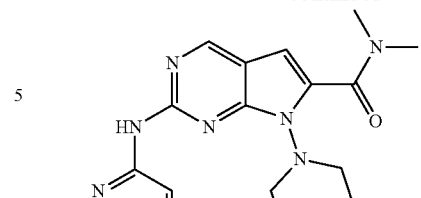
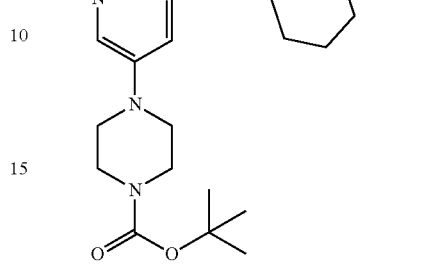
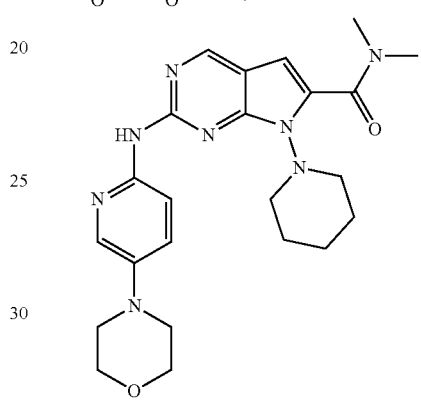
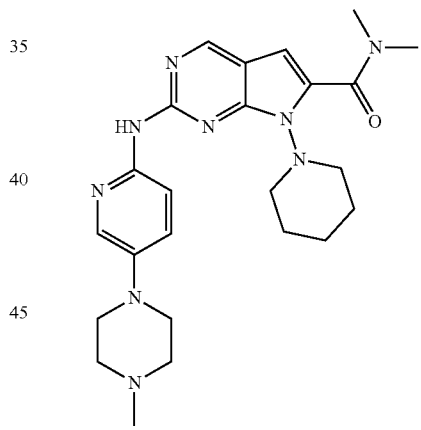
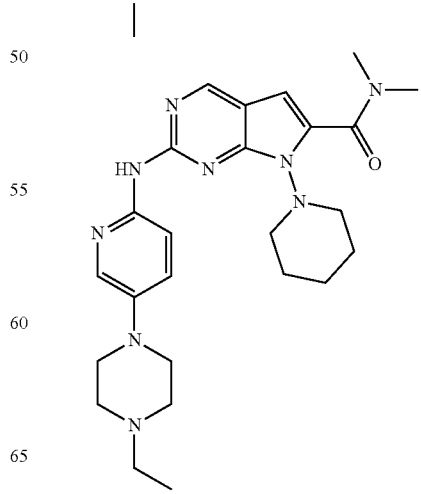

7
-continued
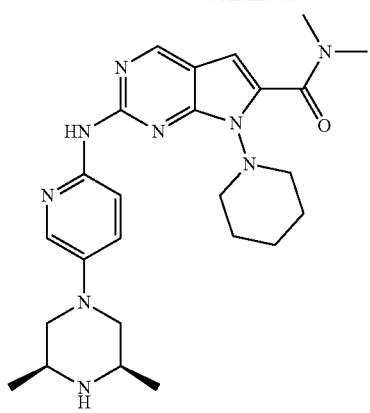
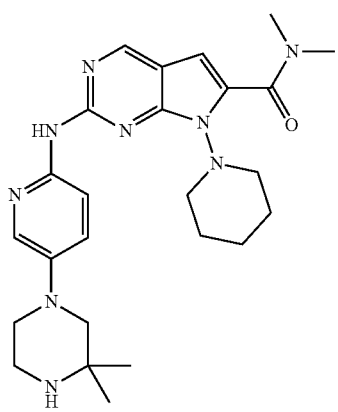
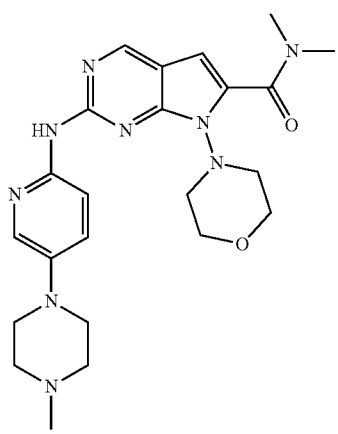
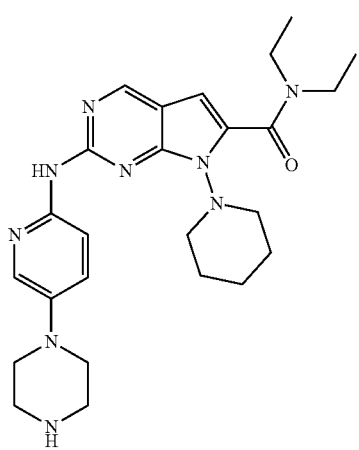
8
-continued
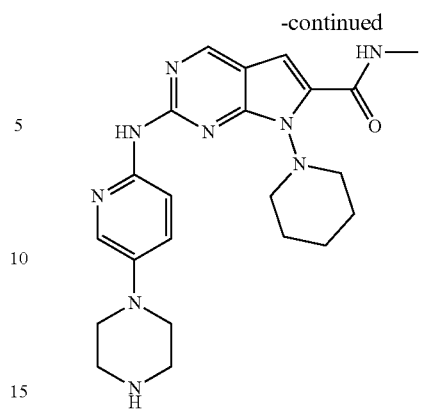
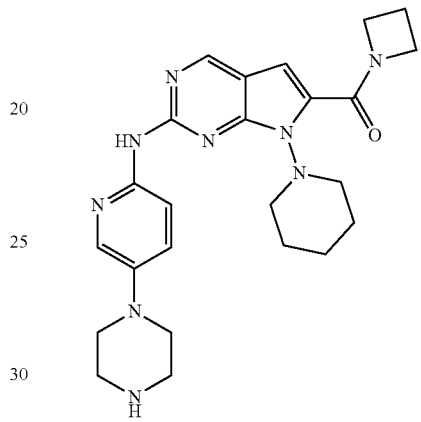
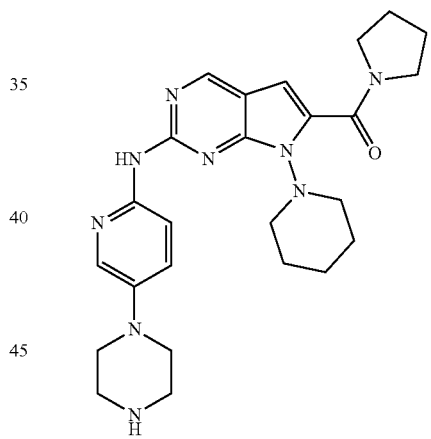
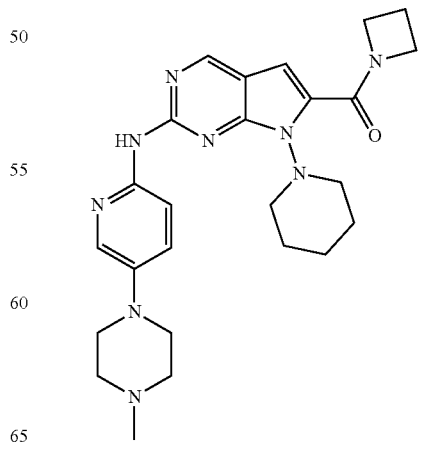

-continued
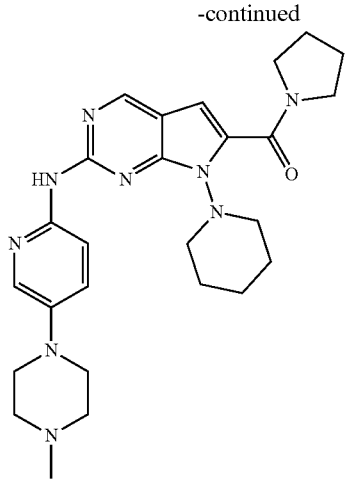
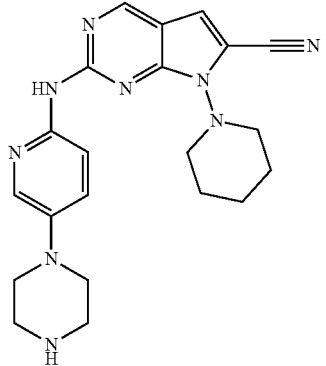
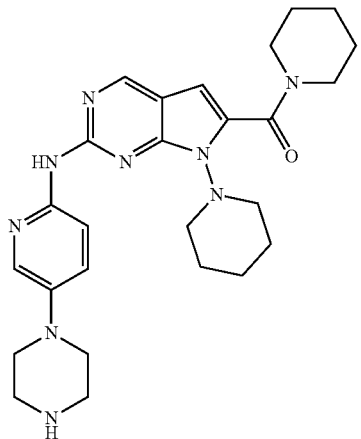
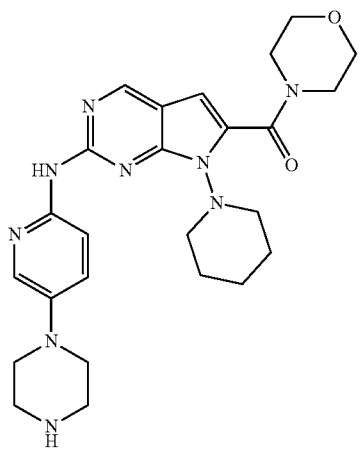
-continued
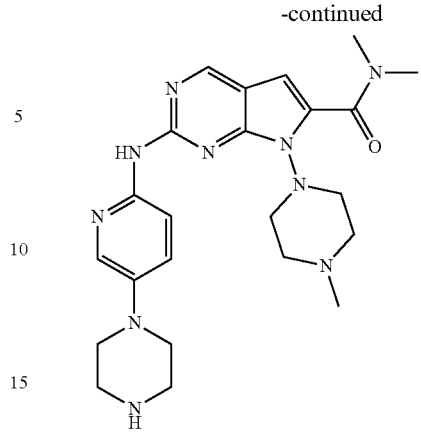
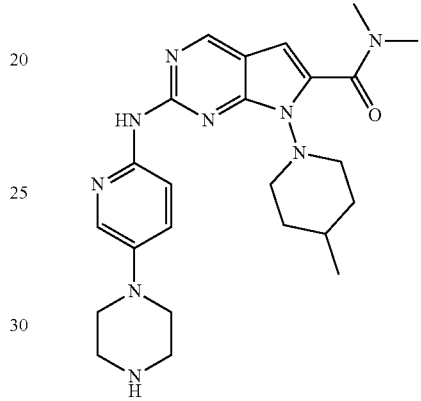
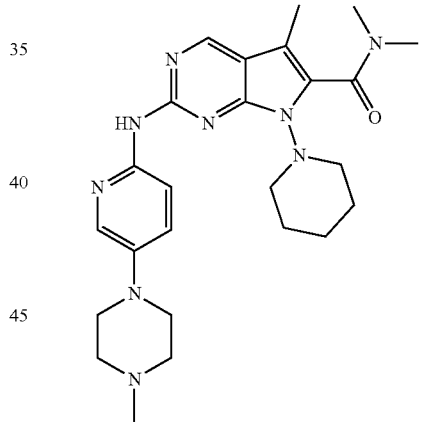
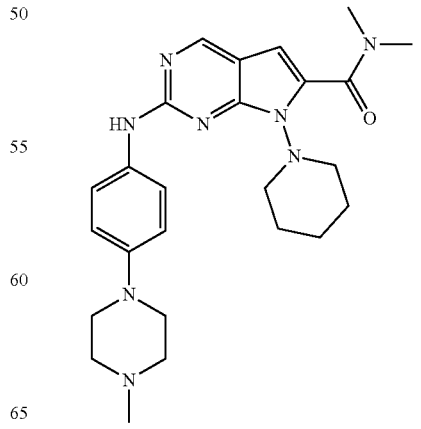

-continued
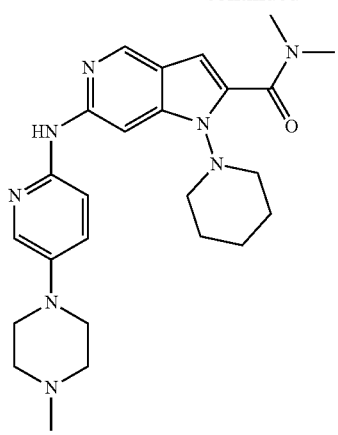
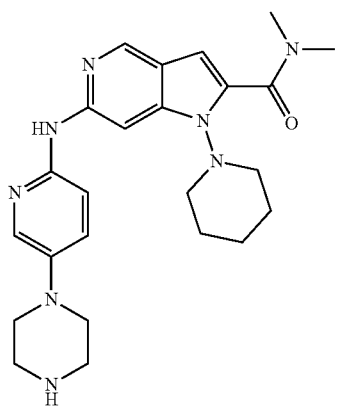
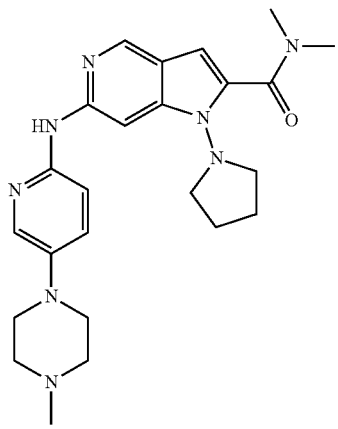
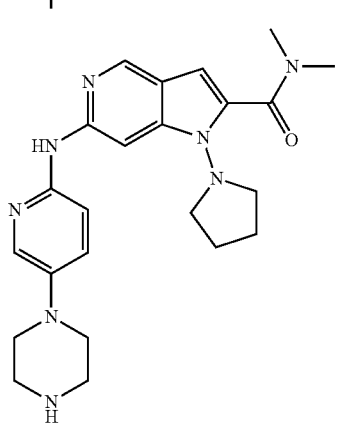
-continued
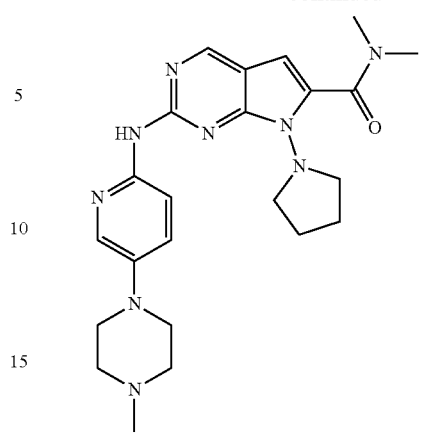
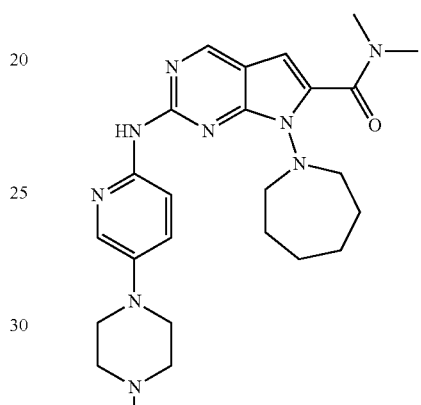
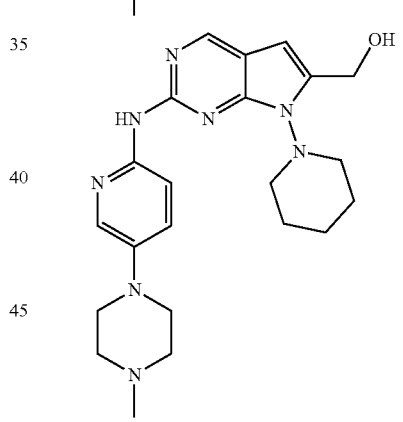
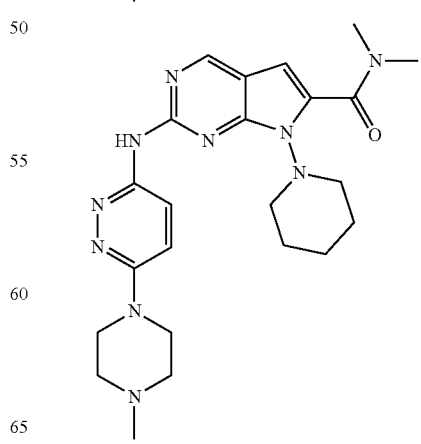

-continued

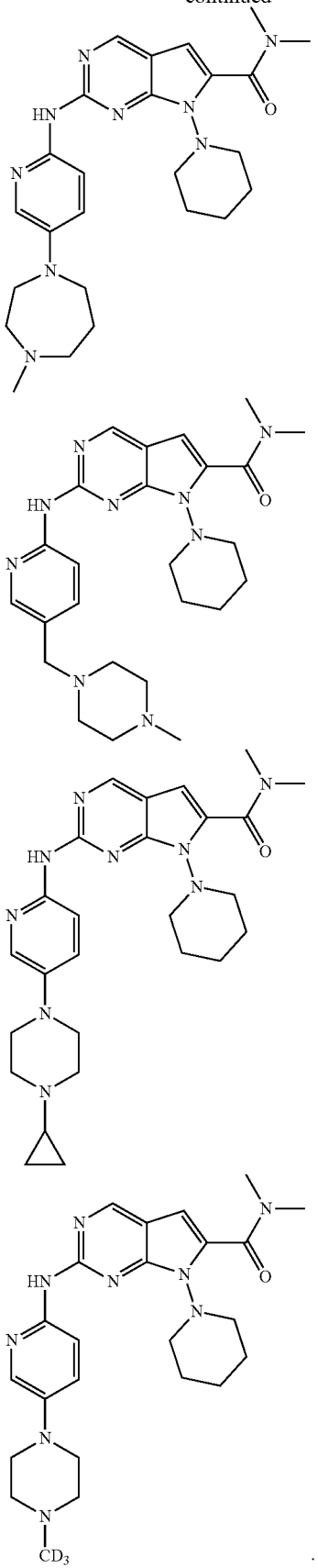

In the second aspect of the present invention, a process for the preparation of the compound of formula I described in the first aspect of the present invention is provided, and the process comprises the following steps:

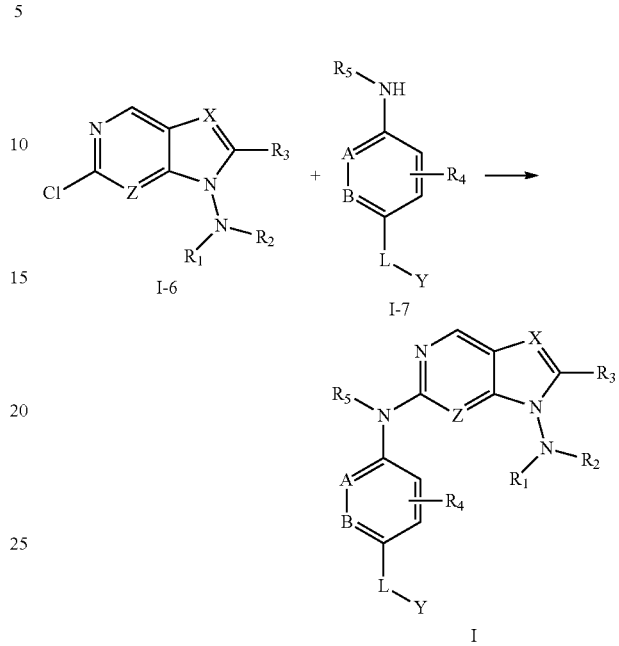

a) a compound of formula I-6 reacts with a compound of formula I-7 in an inert solvent to form a compound of formula I, wherein each group is defined as described above.

In another preferred embodiment, the inert solvent is selected from the group consisting of toluene, xylene, glycol dimethyl ether, dioxane, THF, DMF, DMSO, NMP, or a combination thereof.

In another preferred embodiment, the reaction is carried out in the presence of a palladium catalyst.

In another preferred embodiment, the palladium catalyst is selected from the group consisting of Pd(PPh$_3$)$_4$, Pd$_2$(dba)$_3$, Pd(dba)$_2$, Pd(OAc)$_2$, Pd(PPh$_3$)$_2$Cl$_2$, Pd(dppe)Cl$_2$, Pd(dppf)Cl$_2$, Pd(dppf)Cl$_2$.CH$_2$Cl$_2$, or a combination thereof.

In another preferred embodiment, the reaction is carried out in the presence of a ligand.

In another preferred embodiment, the ligand is a monodentate phosphine ligand or bidentate phosphine ligand; preferably, the ligand is selected from the group consisting of triphenylphosphine, trimethylphenylphosphine, tricyclohexylphosphine, Tri-tert-butylphosphine, X-Phos, S-Phos, Binaphthyl diphenylphosphine, 1,1'-bis(diphenylphosphino) ferrocene, 1,2-bis(diphenylphosphino)ethane, Xant-Phos, or a combination thereof.

In another preferred embodiment, the reaction is carried out in the presence of a base.

In another preferred embodiment, the base is selected from the group consisting of Na$_2$CO$_3$, K$_2$CO$_3$, Cs$_2$CO$_3$, LiHMDS, NaHMDS, KHMDS, sodium tert-butoxide, potassium tert-butoxide, triethylamine, diisopropylamine, diisopropylethylamine, or a combination thereof.

A preferred preparation method comprises the following steps:

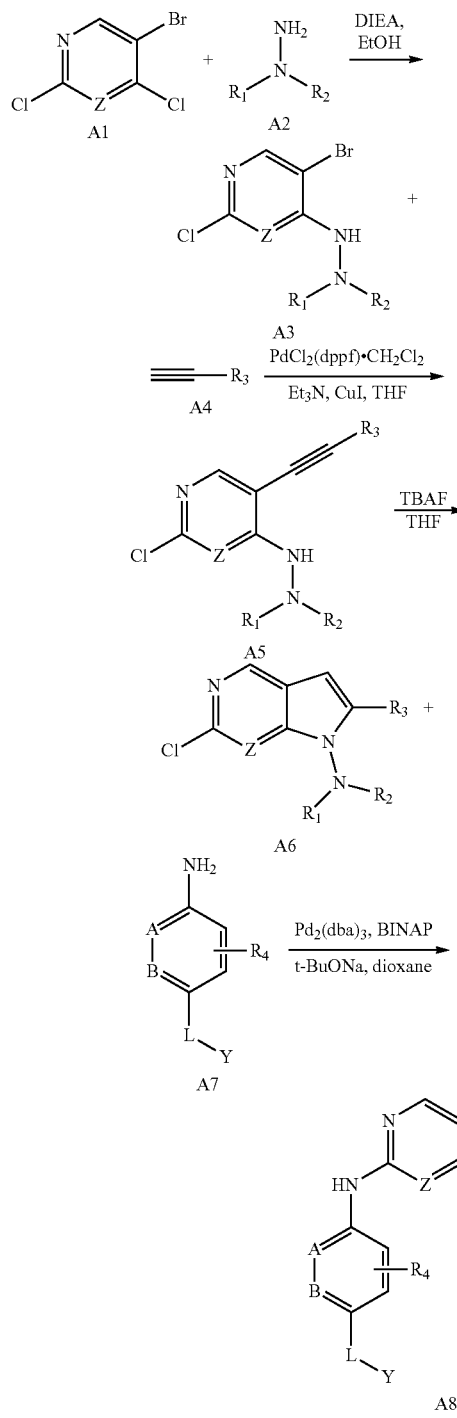

(1) Compound A3 can be obtained by reacting the compound A1 with the corresponding hydrazine A2 in the presence of a base (including but not limited to, diisopropylethylamine, trimethylamine) in an inert solvent (ethanol, THF, etc.).

(2) Compound A5 can be obtained by Sonogashira coupling reaction (reaction time is 2-8 hours) of compound A3 and the corresponding terminal alkyne A4 in an inert solvent (such as THF, DMF, DMSO, dioxane, etc.,) in the presence of a catalyst (e.g., Tetrakis(triphenylphosphine)palladium, Tris(dibenzylideneacetone)dipalladium (Pd2(dba)3), bis (dibenzylideneacetone)palladium, dichlorobis(triphenylphosphine)palladium, bis(tri-o-tolylphosphine)palladium dichloride, 1,2-bis(diphenylphosphino)ethane dichloropalladium, [1,1'-bis(diphenylphosphino)ferrocene] palladium dichloride, [1,1'-bis(diphenylphosphino)ferrocene] dichloromethane dichloromethane complex, etc.), a catalyst b (e.g., cuprous iodide, zinc chloride, silver oxide, silver carbonate, etc.) and an alkali (e.g., potassium carbonate, potassium fluoride, cesium carbonate, cesium fluoride, sodium fluoride, potassium phosphate, potassium hydrated phosphate, sodium carbonate, sodium bicarbonate, 1,8-diazabicyclo[5.4.0]undec-7-ene, triethylamine, diisopropylamine, diisopropylethylamine, pyridine or a combination thereof, etc.);

(3) Compound A6 can be obtained by the reaction of compound A5 in an inert solvent (dichloromethane, THF, acetonitrile, etc.) under heating, with the addition of tetrabutylammonium fluoride (TBAF).

(4) Compound A8 can be obtained by Buchwald-Hartwig coupling reaction (reaction time is 2-8 hours) of compound A6 and the corresponding aromatic amine A7 in an inert solvent (such as toluene, THF, DMF, DMSO, dioxane, etc.), in the presence of a catalyst (such as Tetrakis(triphenylphosphine)palladium, Tris(dibenzylideneacetone)dipalladium (Pd$_2$(dba)$_3$), bis(dibenzylideneacetone)palladium, dichlorobis(triphenylphosphine)palladium, bis(tri-o-tolylphosphine) palladium dichloride, 1,2-bis (diphenylphosphino)ethane dichloropalladium, [1,1'-bis(diphenylphosphino)ferrocene] palladium dichloride, [1,1'-bis(diphenylphosphino)ferrocene]dichloromethane dichloromethane complex, etc.), a ligand (such as trimethylphenylphosphine, tricyclohexylphosphine, tri-tert-butylphosphine, 2,2'-bis(diphenylphosphino)-1,1'-binaphthyl, etc.), and a base (such as potassium carbonate, potassium fluoride, cesium carbonate, cesium fluoride, sodium fluoride, potassium phosphate, potassium hydrated phosphate, sodium carbonate, sodium bicarbonate, sodium tert-butoxide, potassium tert-butoxide, 1,8-diazabicyclo[5.4.0]undec-7-ene, triethylamine, diisopropylamine, diisopropylethylamine, pyridine, or a combination thereof, etc.).

In the third aspect of the present invention, the use of the compound of formula I described in the first aspect of the present invention is provided, the compound of formula I is used for:

(a) preparation of a medicament for the treatment of a disease associated with CDK kinase activity or expression quantity;

(b) preparation of a targeting CDK kinase inhibitor;

(c) non-therapeutic inhibition of CDK kinase activity in vitro;

(d) non-therapeutic inhibition of tumor cell proliferation in vitro; and/or (e) treatment of a disease associated with CDK kinase activity or expression quantity.

In another preferred embodiment, the CDK kinase is selected from the group consisting of CDK4, CDK6, or a combination thereof; and/or
the tumor cell is leukemic cell line, preferably myeloid leukemia cell line, and more preferably acute myeloid leukemia cell line KG1 cell.

In the fourth aspect of the present invention, a pharmaceutical composition is provided, the pharmaceutical composition includes: (i) an effective amount of the compound of formula I, or a pharmaceutically acceptable salt thereof; and (ii) a pharmaceutically acceptable carrier.

In the fifth aspect of the present invention, a method of inhibiting CDK kinase activity is provided, the method comprises step: administering a subject an inhibitory effective amount of a compound of formula I described in the first aspect of the present invention or a pharmaceutically acceptable salt thereof, or administering a subject an inhibitory effective amount of a pharmaceutical composition described in the fourth aspect of the present invention.

In the sixth aspect of the present invention, a method of inhibiting tumor cells in vitro is provided, the method comprises: administering a subject an inhibitory effective amount of a compound of formula I described in the first aspect of the present invention or a pharmaceutically acceptable salt thereof, or administering a subject an inhibitory effective amount of a pharmaceutical composition described in the fourth aspect of the present invention.

It should be understood that each of the above technical features of the invention and each technical feature specifically described below (such as in Examples) can be combined with each other within the scope of the present invention so as to constitute a new or preferred technical solution which needs not be described one by one due to space limitations.

DETAIL DESCRIPTION OF INVENTION

The present inventors have carried out a long-term and intensive study to prepare a class of compounds having a structure represented by formula I and have found that they have inhibitory activities against CDK kinases. The compounds have an inhibitory effect against a series of CDK kinases at very low concentration (can be as low as ≤100 nM), and the inhibitory activities are very excellent, therefore they can be used for the treatment of diseases associated with CDK kinase activity or expression quantity, such as tumors. The inventors have completed the present invention based on the above findings.

Terms

As used herein, the term "C1-C6 alkyl" refers to a straight or branched alkyl having 1 to 6 carbon atoms, for example, methyl, ethyl, propyl, isopropyl, butyl, isobutyl, sec-butyl, tert-butyl or the like.

As used herein, the term "C2-C6 acyl" refers to a straight or branched alkyl-carbonyl having 1 to 6 carbon atoms, for example, acetyl, propionyl, butyryl or the like.

The term "C1-C6 alkylene" refers to a group formed after the C1-C6 alkyl described above has lost one hydrogen atom, such as —$CH_2$—, —$CH_2$—$CH_2$—, or the like.

The term "C6-C10 arylene" refers to a group formed after an aryl having 6 to 10 carbon atoms has lost one hydrogen atom, including monocyclic or bicyclic arylene, such as phenylene, naphthylene, or the like.

The term "six membered aryl" refers to phenyl.

The term "5-8 membered aryl" refers to a carbon-unsaturated system substituent having 5 to 8 membered ring, such as phenyl, or the like.

The term "5-8 membered heteroaryl" refers to an unsaturated ring system substituent having 5 to 8 membered ring system with one or more heteroatoms selected from O, S, N or P, such as pyridyl, thienyl, or the like.

The term "saturated 3-12 membered carbocycle" refers to a saturated carbocyclic ring having 3 to 12 carbon atoms, such as cyclohexyl, or the like.

The term "3-12 membered heterocycle" refers to a saturated ring system substituent having 3 to 12 membered ring system with one or more heteroatoms selected from O, S, N or P, such as piperidinyl, pyrrolyl, or the like.

The term "halogen" refers to F, Cl, Br and I.

In the present invention, the term "contain(s)", "comprise(s)" or "include(s)" means that various ingredients can be used together in the mixtures or compositions of the present invention. Thus, the term "mainly consists of", "consists of" is encompassed by the term "contain(s)".

In the present invention, the term "pharmaceutically acceptable" ingredient is suitable for use in human and/or animals without excessive adverse effects (e.g., toxicity, irritation, and allergic reaction), i.e., a substance with reasonable efficacy/risk ratio.

In the present invention, the term "an effective amount" means an amount of a therapeutic agent that can treat, alleviate or prevent the target disease or condition, or an amount that can exhibit a detectable therapeutic or prevention effect. To a specific subject, the precise effective amount is determined by the subject's body type and health condition, nature and extent of the disease, as well as the selected therapeutic agent and/or combinations of therapeutic agents. Therefore, it is useless to preselect a precise effective amount. However, under a given condition, an effective amount can be ascertained using routine experiments, and a clinician can assess an effective amount.

In the present invention, unless indicated otherwise, the term "substituted" means that one or more hydrogen atoms on a group are substituted with substituent(s) selected from the group consisting of a halogen, an unsubstituted or halogenated C1-C6 alkyl, an unsubstituted or halogenated C2-C6 acyl, and an unsubstituted or halogenated C1-C6 alkylhydroxy.

Unless indicated otherwise, all compounds disclosed in the present invention are intended to include all possible optical isomers, such as the single chiral compound, or the mixtures of various chiral compounds (i.e., racemate). In all of the compounds of the present invention, each chiral carbon atom may optionally be R configuration or S configuration, or a mixture of the R configuration and the S configuration.

As used herein, the term "compound of the invention" refers to the compound of formula I. This term also contains the various crystal forms, the pharmaceutically acceptable salt, hydrate or solvate of the compound of formula I.

As used herein, the term "pharmaceutically acceptable salt" refers to a salt which is suitable for medicine and formed by the compound of the invention and acid or base. Pharmaceutically acceptable salts include inorganic salts and organic salts. A preferred salt is formed by the compound of the invention and acid. The acid suitable for forming salts includes, but not limited to, inorganic acid, such as hydrochloric acid, hydrobromic acid, hydrofluoric acid, sulfuric acid, nitric acid, phosphoric acid, etc.; organic acid, such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzene methanesulfonic acid, benzene sulfonic acid, etc.; and acidic amino acid, such as aspartic acid, glutamic acid and the like.

Pharmaceutical Composition and the Administration Thereof

The compounds of the invention possess outstanding inhibitory activity against CDK kinases such as CDK4, CDK6, therefore, the compounds of the invention and various crystal forms, the pharmaceutically acceptable inorganic or organic salts, hydrate or solvate thereof, and the pharmaceutical compositions comprising compounds of the invention as the main active ingredient, can be used for treating, preventing and alleviating diseases associated with CDK activity or expression quantity. According to the art, the compounds of the invention can be used for treating the following diseases: breast cancer, endometrial cancer, gastric cancer, bladder cancer, lymphoma, head and neck cancer and so on; in particular, can also be combined with PI3K, B-RAF, FGFR and other kinase inhibitors to overcome the kinase inhibitor resistance, and can be used for the treatment of targeted drug resistant melanoma, breast cancer, non-small cell lung cancer, liver cancer, glioma, colon cancer and other tumors.

The pharmaceutical composition of the invention comprises the compound of the invention or pharmaceutically acceptable salt thereof in safe and effective dosage range and pharmaceutically acceptable excipient or carrier. Wherein "safe and effective dosage" refers to the amount of the compound which is enough to improve the patient's condition and would not induce serious side effect. Generally, the pharmaceutical composition contains 1-2000 mg compound of the invention/dose, more preferably, 5 to 200 mg compound of the invention/dose. Preferably, said "one dose" is one capsule or tablet.

"Pharmaceutically acceptable carrier" means: one or more compatible solid or liquid fillers or gel materials, which are suitable for human, and must have sufficient purity and sufficiently low toxicity. "Compatibility" herein means that each component of the composition can be blended with the compound of the invention or with each other, and would not significantly reduce the efficacy of the compound. Some examples of pharmaceutically acceptable carriers include cellulose and the derivatives thereof (such as sodium carboxymethyl cellulose, sodium ethyl cellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerol, mannitol, sorbitol, etc.), emulsifier (such as Tween®), wetting agent (such as sodium dodecyl sulfate), coloring agent, flavoring agent, stabilizer, antioxidant, preservative, pyrogen-free water, etc.

The administration method for the compounds or pharmaceutical compositions of the invention is not specially limited, and the representative administration method includes (but not limited to): oral, intratumor, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with the following components: (a) fillers or compatibilizer, for example, starch, lactose, sucrose, glucose, mannitol and silicic acid; (b) binders, for example, hydroxymethyl cellulose, alginate, gelatin, polyvinylpyrrolidone, sucrose and gum arabic; (c) humectants, such as glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer agents.

The solid dosage forms such as tablets, sugar pills, capsules, pills and granules can be prepared by coating and shell material, such as enteric coatings and other materials known in the art. They can contain opaque agent, and the release of the active compounds or compounds in the compositions can be delayed for releasing in a portion of the digestive tract. Instances of the embedding components can be polymers and waxes. If necessary, the active compounds and one or more above excipients can form microcapsules.

The liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides these inert diluents, the composition may also contain additives such as wetting agents, emulsifiers and suspending agents, sweeteners, flavoring agents and perfumes.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyol and the suitable mixtures thereof.

The dosage forms of compounds of the invention for topical administration include ointments, powders, patches, aerosols, and inhalants. The active ingredients are mixed with physiologically acceptable carriers and any preservatives, buffers, or propellants if necessary, under sterile condition.

The compounds of the invention can be administered alone, or combined with other pharmaceutically acceptable compounds.

When the pharmaceutical compositions are used, safe and effective amount of compounds of the present invention is applied to mammals in need thereof (such as human), wherein the applied dose is the pharmaceutically effective dose. For a person weighted 60 kg, the daily dose is usually 1~2000 mg, preferably 5~500 mg. Of course, the particular dose should also depend on other factors, such as the route of administration, patient healthy status, which are within the skill of a skilled physician.

Compound of Formula I

The present invention provides a compound of formula I, or a pharmaceutically acceptable salt thereof:

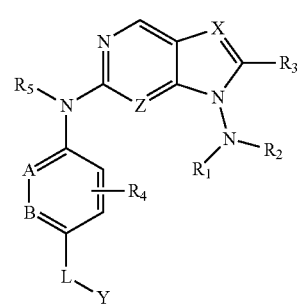

I wherein,

R₁ and R₂ are each independently selected from H, a substituted or unsubstituted C1-C8 alkyl, C(O)OR₈, CONR₉R₁₀, C(O)R₁₁, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

in addition, R₁ and R₂ can be connected with adjacent N atom to form a ring structure, said ring structure includes a substituted or unsubstituted 3-12 membered saturated or unsaturated heterocycle or a bridged ring or a spiro ring; wherein said heterocycle refers to a ring structure containing 0-3 heteroatoms selected from the group consisting of N, O or S, in addition to the nitrogen atom attached to the parent nucleus;

R₃ is selected from a substituted or unsubstituted C1-C8 alkyl, CN, C(O)OR₁₂, CONR₁₃R₁₄, C(O)R₁₅, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

R₄ is selected from H, a substituted or unsubstituted C1-C4 alkyl, a substituted or unsubstituted C1-C8 alkoxy, a halogen, OH, CN, C(O)OR₁₂, CONR₁₃R₁₄, C(O)R₁₅, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

R₅ is selected from H or C1-C4 alkyl;

X is CR₁₆ or N;

A, B, and Z are each independently selected from N or CR₁₆;

R₁₆ is H, C1-C4 alkyl or C1-C4 haloalkyl;

L is selected from the group consisting of none, C1-C6 alkylene, C(O), CONR₁₇ or S(O)₂;

Y is H, R₁₈, NR₁₉R₂₀, OH, or Y is selected from part of the group consisting of:

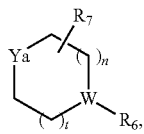

wherein,

R₆ is none, H, a substituted or unsubstituted C1-C8 alkyl, a substituted or unsubstituted C1-C8 alkoxy, a substituted or unsubstituted C2-C6 acyl, a substituted or unsubstituted C2-C6 sulfonyl, a substituted or unsubstituted C1-C6 alkylenehydroxy, CONR₂₂R₂₃ or C(O)R₂₄;

R₇ may be 0-3 substituents and R₇ is a substituted or unsubstituted C1-C8 alkyl, an oxygen or a halogen, or two or more R₇ form a bridged cycloalkyl; W is CR₂₁, N or O (when W is O, R₆ is absent);

Ya is CR₂₁ or N; R₂₁ is H or a halogen;

R₈, R₉, R₁₀, R₁₁, R₁₂, R₁₃, R₁₄, R₁₅, R₁₇, R₁₈, R₁₉, R₂₀, R₂₂, R₂₃ and R₂₄ are each independently selected from H, a substituted or unsubstituted C1-C8 alkyl, a substituted or unsubstituted C1-C8 alkoxy, a substituted or unsubstituted C1-C6 alkyleneamino, a substituted or unsubstituted C1-C6 alkylenehydroxy, a substituted or unsubstituted 5-8 membered aryl, a substituted or unsubstituted 5-8 membered heteroaryl, a substituted or unsubstituted 3-12 membered saturated heterocycle or carbocycle; wherein said heteroaryl contains at least one heteroatom selected from the group consisting of N, O or S, said heterocycle contains at least one heteroatom selected from the group consisting of N, O or S;

n and t are 0, 1 or 2, respectively;

any one of the above mentioned "substituted" means that one or more hydrogen atoms on the group are substituted with substituent(s) selected from the group consisting of a halogen, OH, NH₂, CN, an unsubstituted or halogenated C1-C8 alkyl, C1-C8 alkoxy, an unsubstituted or halogenated C2-C6 alkenyl, an unsubstituted or halogenated C2-C6 alkynyl, an unsubstituted or halogenated C2-C6 acyl, an unsubstituted or halogenated 5-8 membered aryl, an unsubstituted or halogenated 5-8 membered heteroaryl, an unsubstituted or halogenated 3-12 membered saturated heterocycle or carbocycle; wherein said heteroaryl contains 1-3 heteroatoms selected from the group consisting of N, O or S, said heterocycle contains 1-3 heteroatoms selected from the group consisting of N, O or S.

In another preferred embodiment,

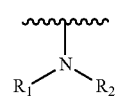

is a substituted or unsubstituted group selected from the group consisting of

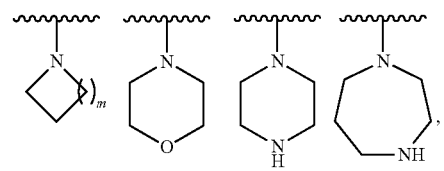

wherein m is 0, 1, 2, 3, 4, 5, 6, 7, 8 or 9, and said "substituted" is as described above.

In another preferred embodiment, R₁ and R₂, together with the adjacent nitrogen atom, form a 4-12 membered ring structure.

In another preferred embodiment, R₁ and R₂, together with the adjacent nitrogen atom, form a 5-7 membered ring structure.

In another preferred embodiment, R₁ and R₂, together with the adjacent nitrogen atom, form a 6 membered ring structure.

In another preferred embodiment, R₁₃ and R₁₄, together with the adjacent nitrogen atom, form a 4-6 membered ring structure.

In another preferred embodiment, when L is none, Y is a 6 membered heterocycle containing nitrogen atom.

In another preferred embodiment, A, B, L, X, Y, Z, R₁, R₂, R₃, R₄ or R₅ are the corresponding group in the specific compounds described in the examples.

In another preferred embodiment, the compound of formula I is a compound as shown below:

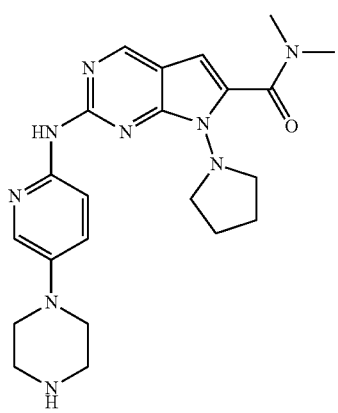
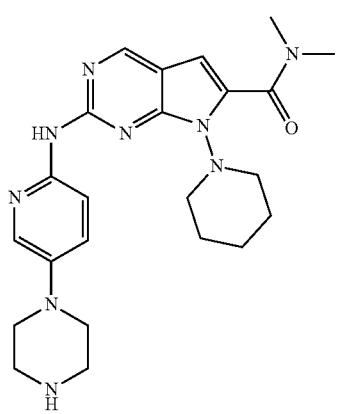
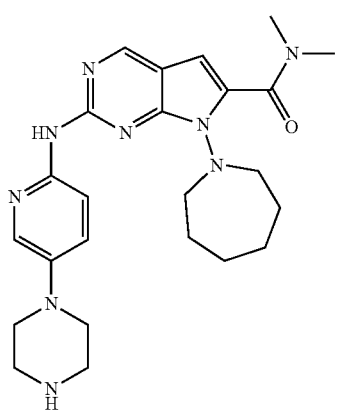
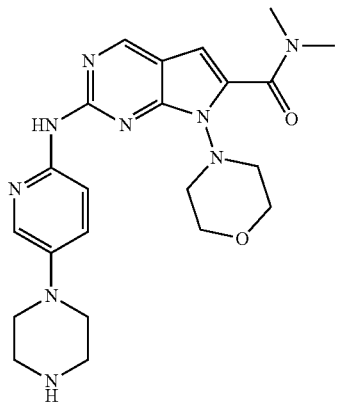
-continued
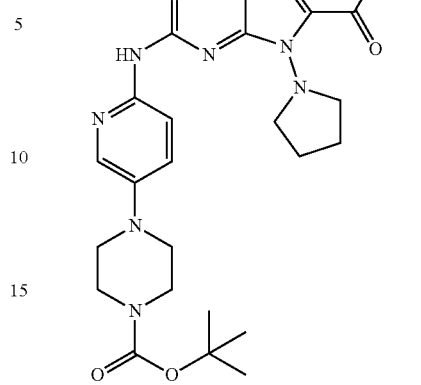
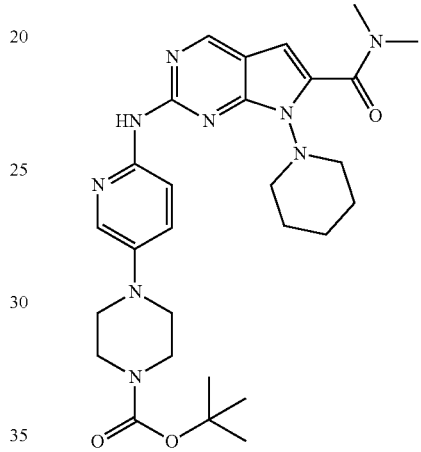
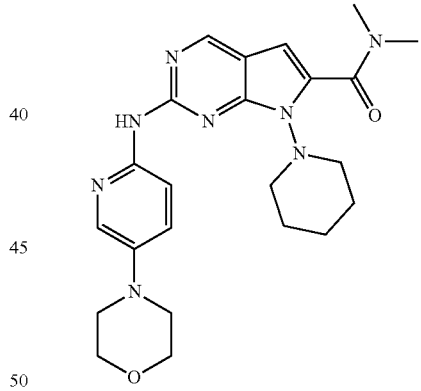
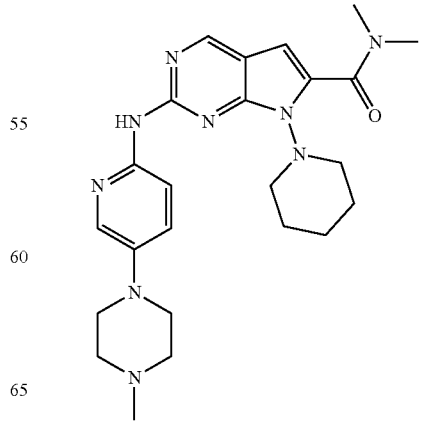

-continued
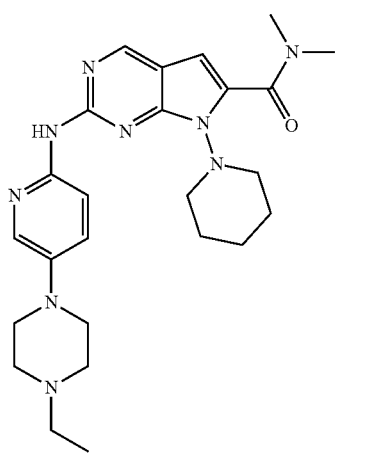
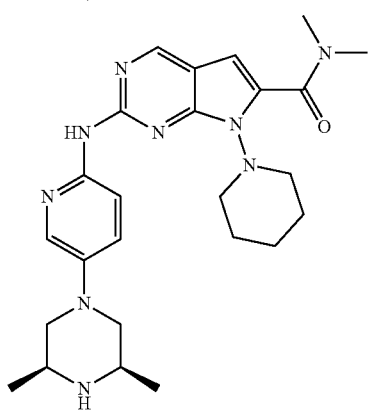
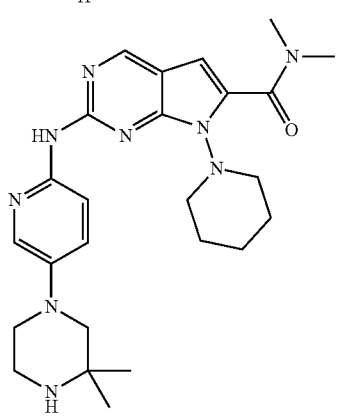
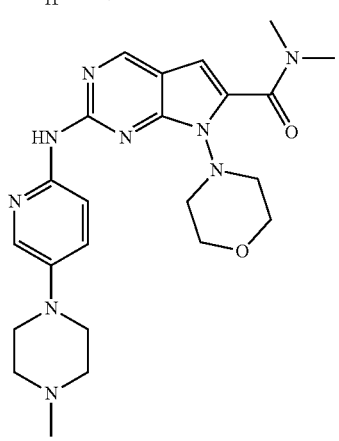
-continued
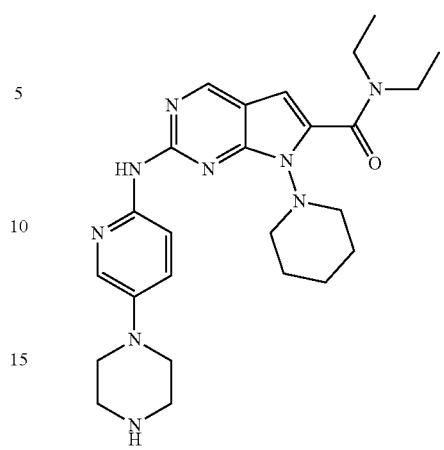
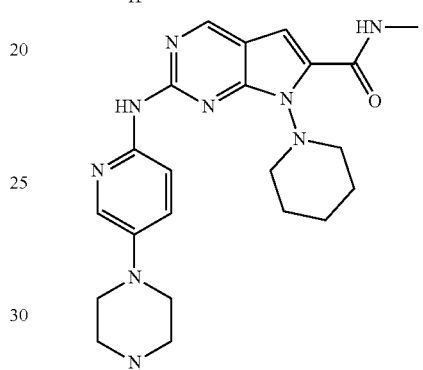
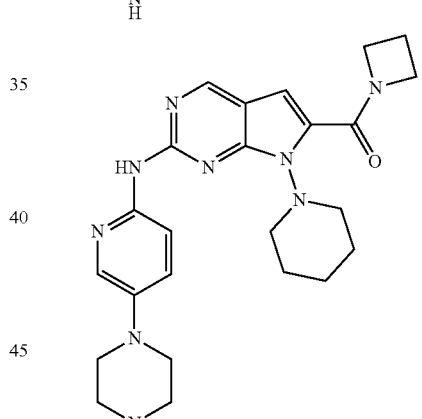
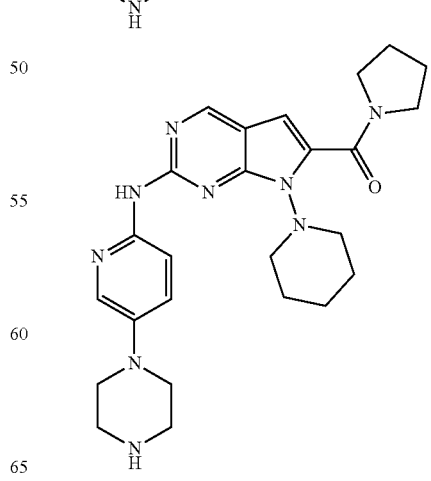

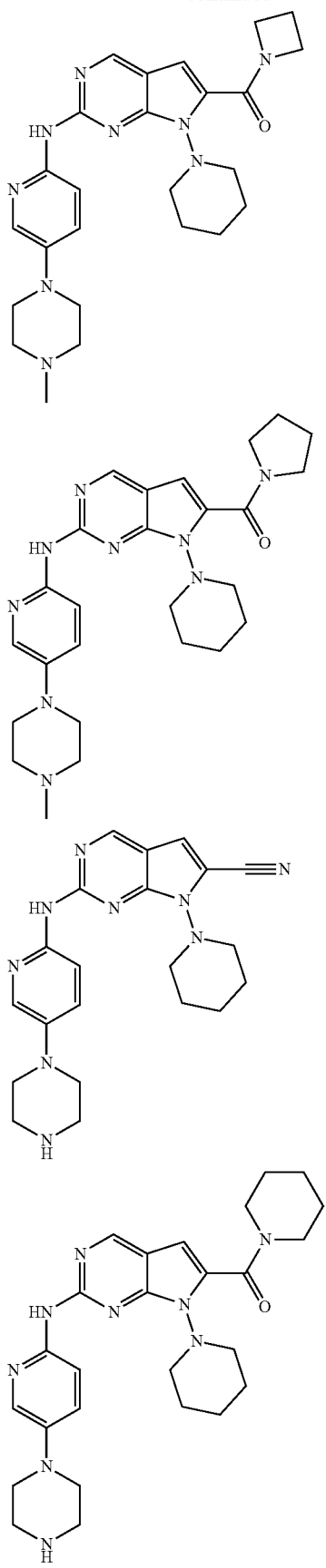
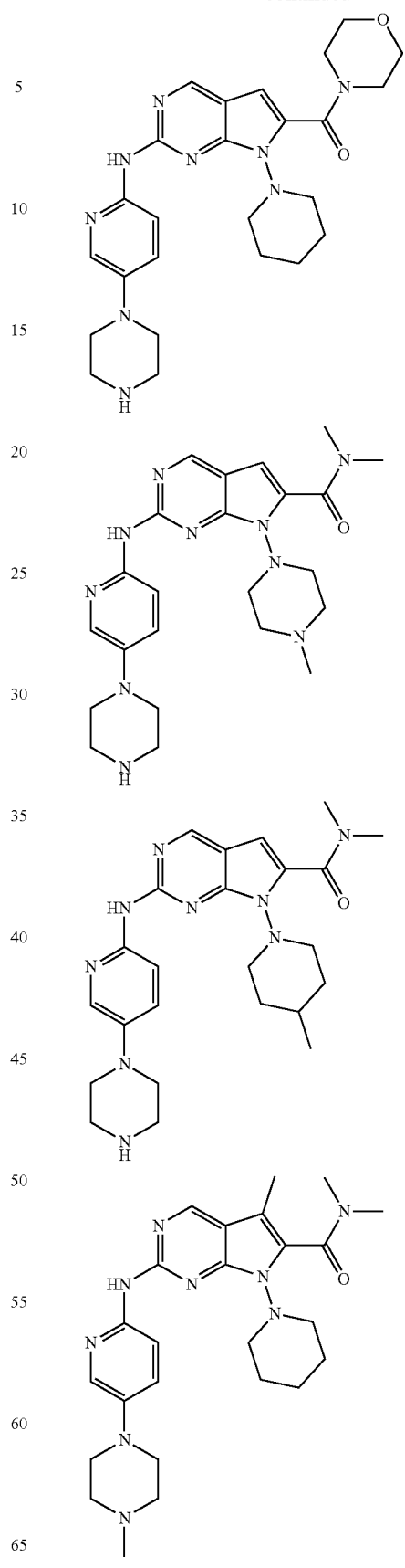

-continued
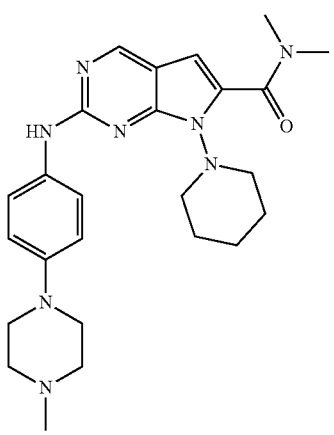
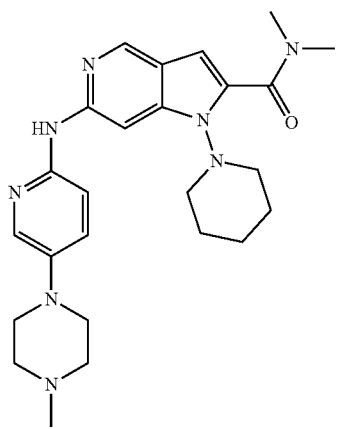
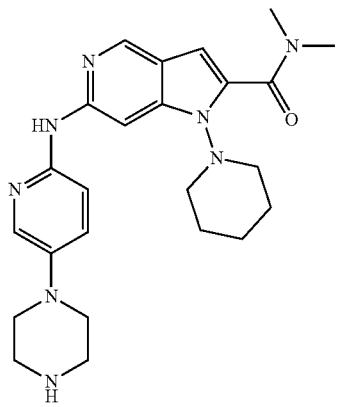
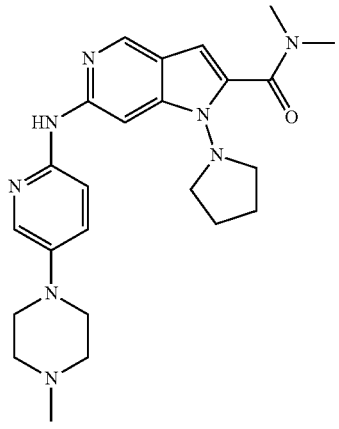
-continued
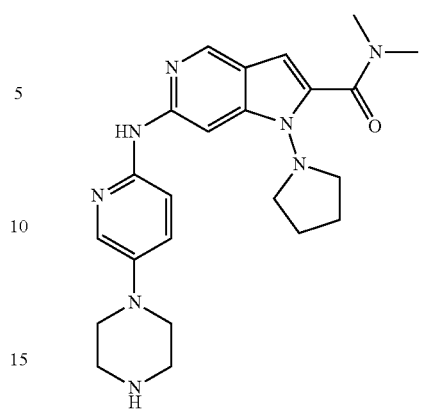
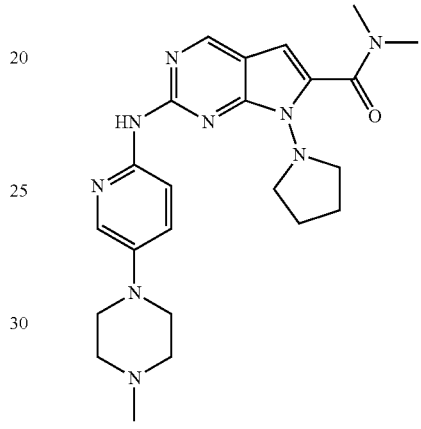
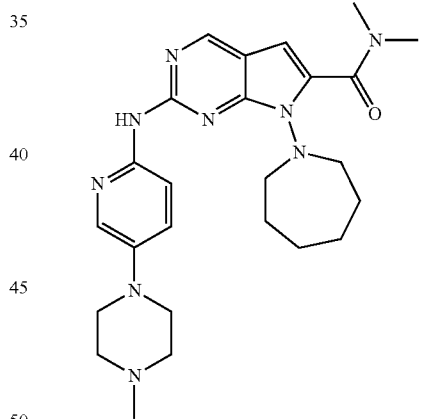
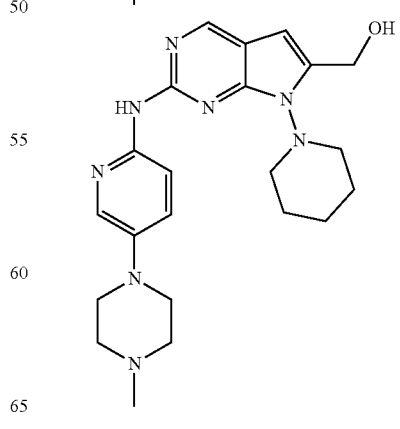

-continued

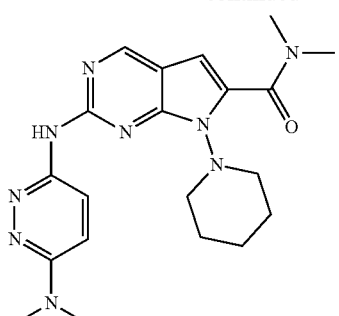

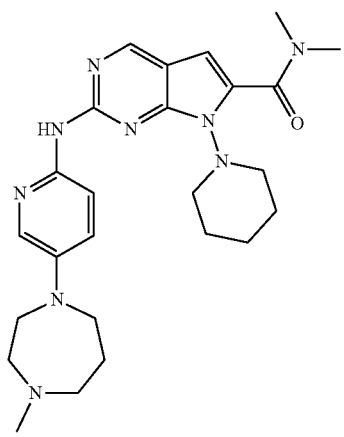

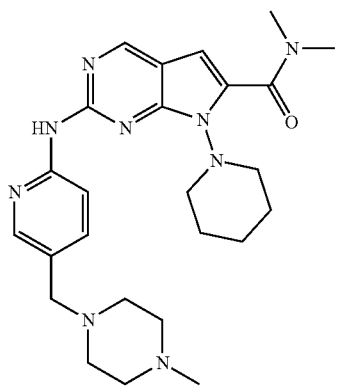

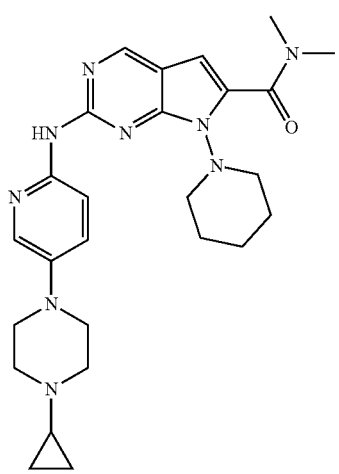

-continued

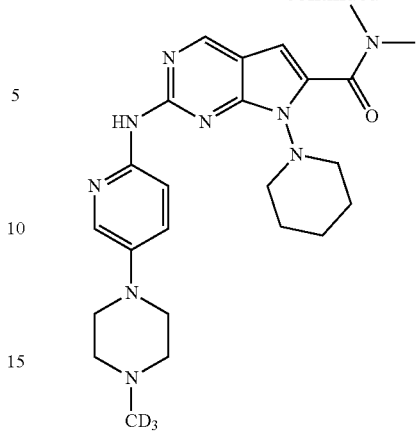

Process for the Preparation of the Compound of Formula I

The present invention provides a process for the preparation of the compound of formula I, the process comprises the following step:

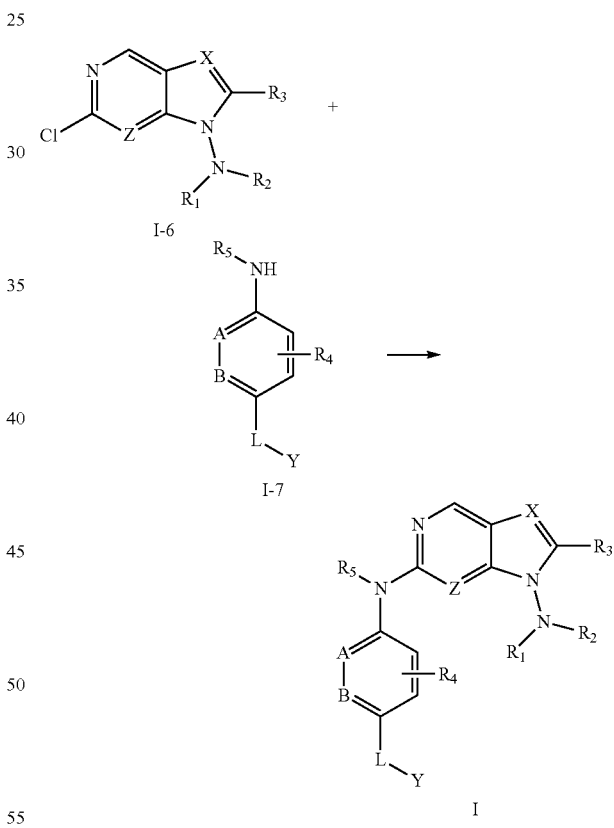

a) a compound of formula I-6 reacts with a compound of formula I-7 in an inert solvent to form the compound of formula I, wherein each group is as defined above.

In another preferred embodiment, the inert solvent is selected from the group consisting of toluene, xylene, glycol dimethyl ether, dioxane, THF, DMF, DMSO, NMP, or a combination thereof.

In another preferred embodiment, the reaction is carried out in the presence of a palladium catalyst.

In another preferred embodiment, the palladium catalyst is selected from the group consisting of Pd(PPh$_3$)$_4$, Pd$_2$(dba)$_3$, Pd(dba)$_2$, Pd(OAc)$_2$, Pd(PPh$_3$)$_2$Cl$_2$, Pd(dppe)Cl$_2$, Pd(dppf)Cl$_2$, Pd(dppf)Cl$_2$·CH$_2$Cl$_2$, or a combination thereof.

In another preferred embodiment, the reaction is carried out in the presence of a ligand.

In another preferred embodiment, the ligand is a monodentate phosphine ligand or bidentate phosphine ligand; preferably, the ligand is selected from the group consisting of triphenylphosphine, trimethylphenylphosphine, tricyclohexylphosphine, Tri-tert-butylphosphine, X-Phos, S-Phos, Binaphthyl diphenylphosphine, 1,1'-bis(diphenylphosphino)ferrocene, 1,2-bis(diphenylphosphino)ethane, Xant-Phos, or a combination thereof.

In another preferred embodiment, the reaction is carried out in the presence of a base.

In another preferred embodiment, the base is selected from the group consisting of Na$_2$CO$_3$, K$_2$CO$_3$, Cs$_2$CO$_3$, LiHMDS, NaHMDS, KHMDS, sodium tert-butoxide, potassium tert-butoxide, triethylamine, diisopropylamine, diisopropylethylamine, or a combination thereof.

A preferred preparation method comprises the following steps:

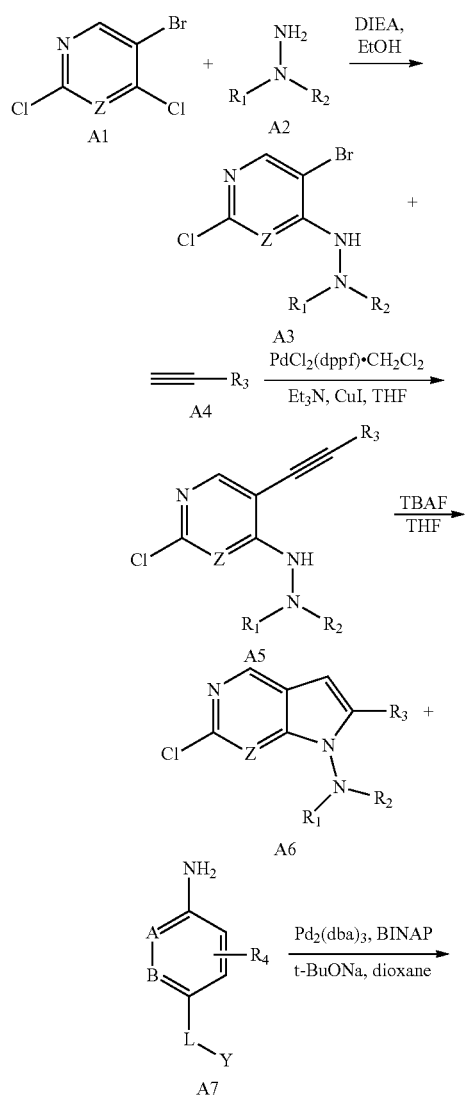

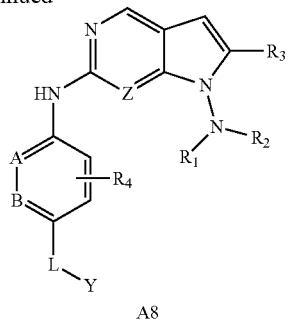

(1) Compound A3 can be obtained by reacting the compound A1 with the corresponding hydrazine A2 in the presence of a base (such as, but not limited to, diisopropylethylamine, trimethylamine) in an inert solvent (ethanol, THF, etc.).

(2) Compound A5 can be obtained by Sonogashira coupling reaction (reaction time is 2-8 hours) of compound A3 and the corresponding terminal alkyne A4 in an inert solvent (such as THF, DMF, DMSO, dioxane, etc.,) in the presence of a catalyst (e.g., Tetrakis(triphenylphosphine)palladium, Tris(dibenzylideneacetone)dipalladium (Pd2(dba)3), bis(dibenzylideneacetone) palladium, dichlorobis(triphenylphosphine) palladium, bis(triphenylbenzene)methylphosphine)palladium dichloride, 1,2-bis (diphenylphosphino)ethane dichloropalladium, [1,1'-bis(diphenylphosphino)ferrocene] palladium dichloride, [1,1'-bis(diphenylphosphino)ferrocene] dichloromethane dichloromethane complex, etc.), a catalyst b (e.g., cuprous iodide, zinc chloride, silver oxide, silver carbonate, etc.) and an alkali (e.g., potassium carbonate, potassium fluoride, cesium carbonate, cesium fluoride, sodium fluoride, potassium phosphate, potassium hydrated phosphate, sodium carbonate, sodium bicarbonate, 1,8-diazabicyclo[5.4.0]undec-7-ene, triethylamine, diisopropylamine, diisopropylethylamine, pyridine or a combination thereof, etc.);

(3) Compound A6 can be obtained by the reaction of compound A5 in an inert solvent (dichloromethane, THF, acetonitrile, etc.) under heating, with the addition of tetrabutylammonium fluoride (TBAF).

(4) Compound A8 can be obtained by Buchwald-Hartwig coupling reaction (reaction time is 2-8 hours) of compound A6 and the corresponding aromatic amine A7 in an inert solvent (such as toluene, THF, DMF, DMSO, dioxane, etc.), in the presence of a catalyst (such as Tetrakis(triphenylphosphine)palladium, Tris(dibenzylideneacetone)dipalladium (Pd$_2$(dba)$_3$), bis(dibenzylideneacetone)palladium, dichlorobis(triphenylphosphine)palladium, bis(tri-o-tolylphosphine) palladium dichloride, 1,2-bis (diphenylphosphino)ethane dichloropalladium, [1,1'-bis(diphenylphosphino)ferrocene] palladium dichloride, [1,1'-bis(diphenylphosphino)ferrocene] dichloromethane dichloromethane complex, etc.), a ligand (such as trimethylphenylphosphine, tricyclohexylphosphine, tri-tert-butylphosphine, 2,2'-bis(diphenylphosphino)-1,1'-binaphthyl, etc.), and a base (such as potassium carbonate, potassium fluoride, cesium carbonate, cesium fluoride, sodium fluoride, potassium phosphate, potassium hydrated phosphate, sodium carbonate, sodium bicarbonate, sodium tert-butoxide, potassium tert-butoxide, 1,8-diazabicyclo[5.4.0]undec-7-ene, triethylamine, diisopropylamine, diisopropylethylamine, pyridine, or a combination thereof, etc.,).

Use of the compound of formula I

The present invention provides use of the compound of formula I, the compound of formula I is used for:

(a) preparation of a medicament for the treatment of a disease associated with CDK kinase activity or expression quantity;

(b) preparation of a targeting CDK kinase inhibitor;

(c) non-therapeutic inhibition of CDK kinase activity in vitro;

(d) non-therapeutic inhibition of tumor cell proliferation in vitro; and/or (e) treatment of a disease associated with CDK kinase activity or expression quantity.

In another preferred embodiment, the CDK kinase is selected from the group consisting of CDK4, CDK6, or a combination thereof; and/or the tumor cell is leukemic cell line, preferably myeloid leukemia cell line, and more preferably acute myeloid leukemia cell line KG1 cell.

The main advantages of the present invention include:

1. providing a compound of formula I.

2. providing a novel CDK kinase inhibitor and its preparation and application, and the inhibitor can inhibit activities of various types of CDK kinases at very low concentration.

3. providing a pharmaceutical composition for the treatment of diseases associated with CDK kinase activity.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

In each example:

LCMS instrument: PumpAgilent1100UV detector: Agilent1100DAD;

MassSpectrometer: API3000;

chromatographic column: WaterssunfireC18, 4.6×50 mm, 5um;

mobile phase: A—acetonitrile; B—H$_2$O (0.1% FA).

EXAMPLE 1

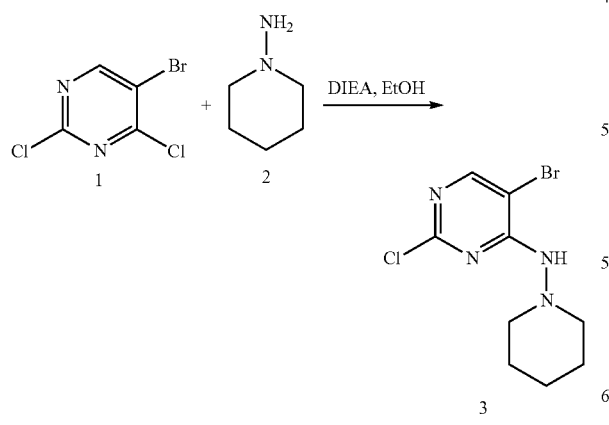

Compound 1 (5.00 g, 21.94 mmol) and ethanol (100.0 mL) were added into a dried 250 mL, 3-neck flask, and 1-aminopiperidine 2 (3.30 g, 32.91 mmol) and N,N-Diisopropylethylamine (4.25 g, 32.91 mmol) were then added dropwise slowly at −20° C. The reaction system was stirred at −20° C. for 3 hours, and then the reaction solution was evaporated and purified by silicagel column to obtain compound 3 (2.9 g, 45.24%) as a white solid. LCMS: 293 (M+H)+, RT=0.50 mim.

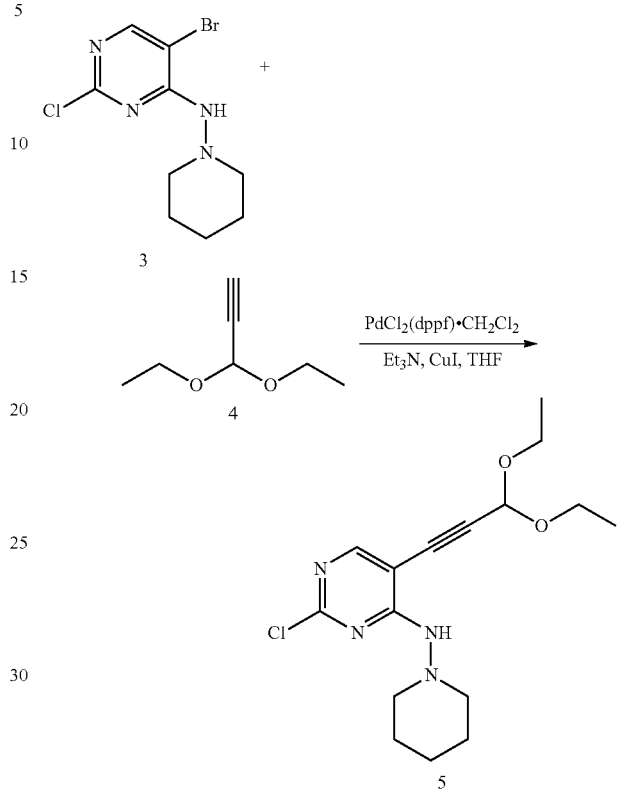

Compound 3 (2.5 g, 8.56 mmol) and [1,1'-Bis(diphenylphosphino)ferrocene]-palladium(II) dichloride-dichloromethane complex (0.35 g, 0.4281 mmol) were dissolved in tetrahydrofuran (12 mL), trimethylamine (1.3 g, 12.84 mmol) and 3,3-diethoxy-1-propyne 4 (1.64 g, 12.84 mmol) were then added at room temperature. The air of reaction system was replaced by nitrogen for 1 minute, and the reaction system was stirred at room temperature for 10 minutes. Copper iodide (65.1 mg, 0.3425 mmol) was then added, and the air was replaced by nitrogen for three times. The reaction system was reacted under microwave at 100° C. for 6 hours. The mixture was mixed with silica gel and purified by column to obtain compound 5 (1.512 g, 52.25%1 as a yellow oil. LCMS: 339 (M+H)+, RT=1.72 mim.

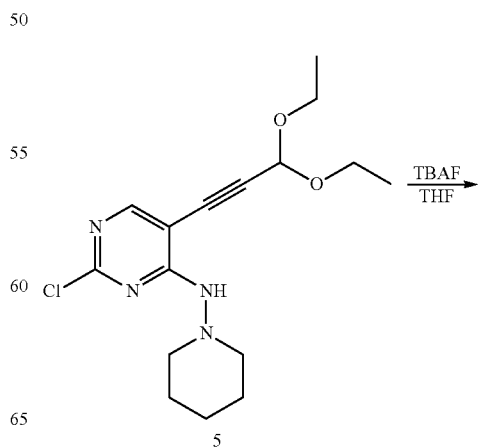

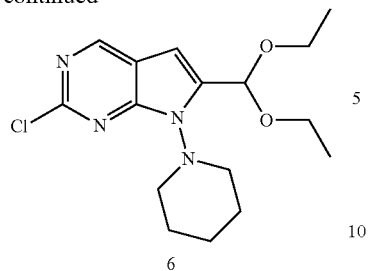

6

Compound 5 (1.512 g, 4.47 mmol) was dissolved in tetrahydrofuran (80 mL). Tetrabutylammonium fluoride (7.13 g, 27.29 mmol) was added at room temperature. The reaction system was stirred at 65° C. for 2 hours, and then the reaction solution was evaporated and purified by silicagel column to obtain compound 6 (1.208 g, 79.89%) as a yellow oil. LCMS: 339 (M+H)+, RT=1.72 mim.

¹HNMR (CD₃Cl3, 400 MHz) δ (ppm) 8.723 (s, 1H), 6.512 (s, 1H), 5.728 (s, 1H), 3.967 (t, 2H, J=11 Hz), 3.646-3.729 (m, 4H), 3.104 (d, 2H, J=10 Hz), 1.689-1.838 (m, 6H), 1.261 (t, 6H, J=7 Hz).

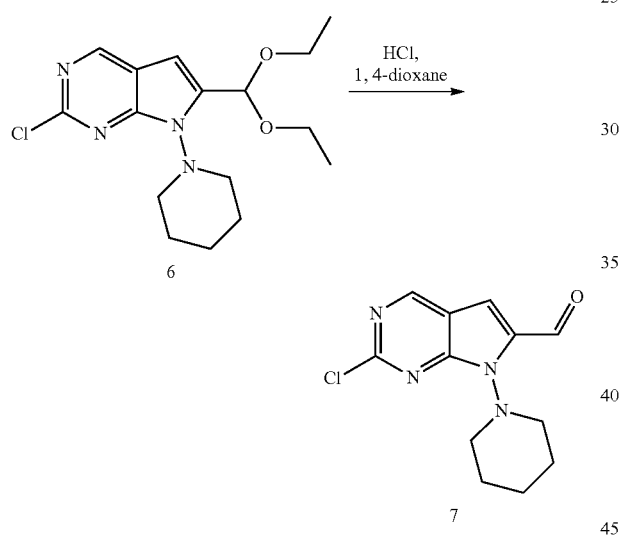

Compound 6 (0.98 g, 2.899 mmol) was dissolved in 1,4-dioxane (15 mL), and concentrated hydrochloric acid (8 mL) was added at room temperature. The reaction system was stirred for 10 minutes and diluted with water (60 mL), and then extracted with ethyl acetate (80 mL) twice. The organic phase was combined, dried over anhydrous Na₂SO₄, and evaporated to give compound 7 (0.765 g, 100%) as a brown solid which was used for the next step without purification. LCMS: 265 (M+H)+, RT=1.34 mim.

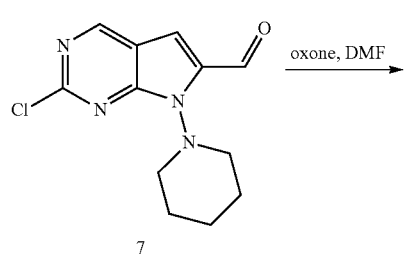

7

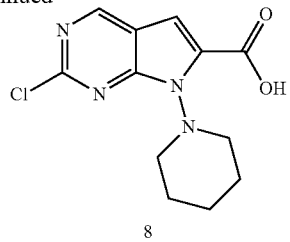

8

Compound 7 (0.765 g, 2.899 mmol) was dissolved in N,N-dimethylformamide (5 mL), and potassium peroxomonosulfate (1.96 g, 3.1875 mmol) was added at room temperature. The reaction system was stirred at room temperature overnight. Water was added into the reaction solution, solid was precipitated and filtered to obtain compound 8 (0.812 g, 100%) as a yellow solid. LCMS: 281 (M+H)+, RT=0.92 mim.

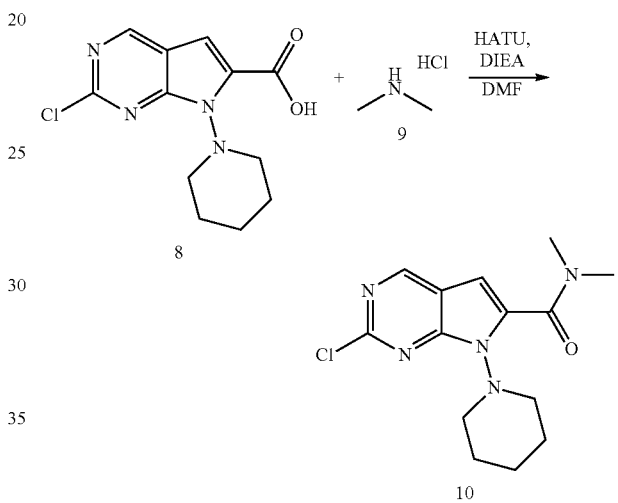

Compound 8 (0.54 g, 1.929 mmol) and dimethylamine hydrochloride 9 (0.189 g, 2.3143 mmol) were dissolved in N,N-dimethylformamide (6 mL), and 2-(7-azobenzotriazol)-N,N,N',N'-tetramethyluronium hexafluorophosphate (0.733 g, 1.929 mmol) and N,N-diisopropylethylamine (0.784 g, 5.786 mmol) were added at room temperature. The reaction system was stirred for 1 hour. The reaction solution was evaporated by oil pump and purified by silicagel column to obtain compound 10 (0.118 g, 19.93%) as a yellow solid. LCMS: 308 (M+H)+, RT=1.42 mim.

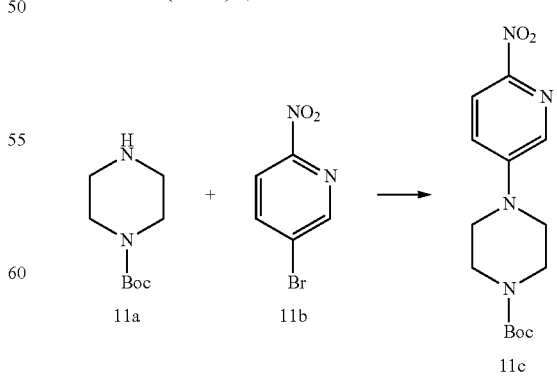

Compound 11a (13.7 g, 73.9 mmol), compound 11b (10 g, 49.3 mmol), potassium iodide (81.8 mg, 0.493 mmol) and potassium carbonate (13.6 g, 98.6 mmol) were added into DMSO (100 mL). The reaction solution was stirred at 120° C. overnight and then cooled to room temperature, adjusted to pH 7 with hydrochloric acid (1 mol) and then extracted with dichloromethane. The aqueous phase was alkalize by saturated solution of sodium carbonate, and then extracted with dichloromethane again. The organic phase was combined and dried over anhydrous $Na_2SO_4$, concentrated and then slurried by water to give compound 11c (9.2 g, 60%). LCMS: 309 (M+H)+, RT=1.710 min.

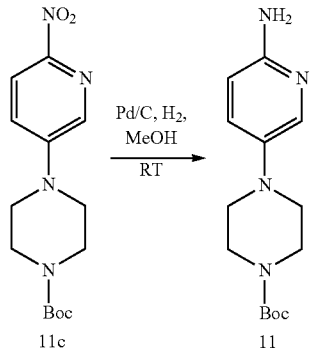

Compound 11c (9.2 g, 29.9 mmol) and wet palladium carbon (2 g) were added into methanol (100 mL), the air in reaction solution was replaced by hydrogen for four to five times, and then the reaction system was stirred under hydrogen atmosphere at room temperature overnight. The reaction solution was filtered, the filter cake was washed with a little methanol, the filtrate was concentrated to give compound 11 (7.1 g, 85%). LCMS: 279 (M+H)+, RT=1.120 min.

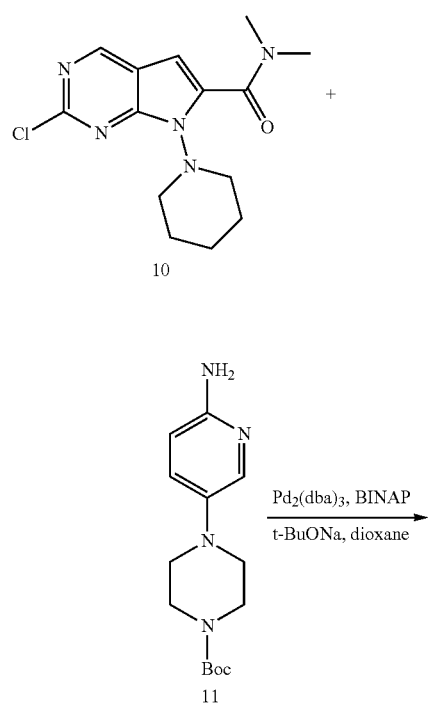

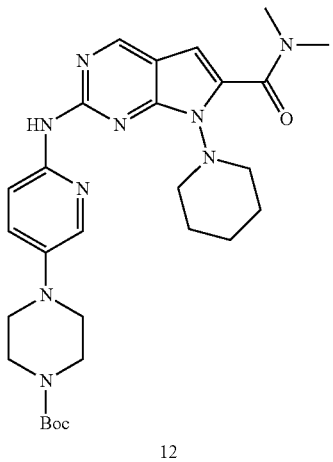

Compound 10 (90 mg, 0.2932 mmol), 4-(6-aminopyridin-3-yl) piperazine-1-carboxylic acid tert-butyl ester 11 (122.2 mg, 0.4397 mmol) and Tris(dibenzylideneacetone)dipalladium (26.8 mg, 0.02932 mmol) were dissolved in 1,4-dioxane (1 mL), and then sodium tert-butoxide (50.7 mg, 0.5277 mmol) and Bis(diphenylphosphino)-1,1'-binaphthalene (36.5 mg, 0.05863 mmol) were added, replaced by nitrogen for three times. The reaction system was reacted under microwave at 110° C. for 1.5 hours. The mixture was evaporated and purified to give compound 12 (68 mg, 42.3%) as a brown solid. LCMS: 550 (M+H)+, RT=1.41 mim.

$^1$HNMR (CDCl3,400 MHz) δ (ppm) 8.931 (s, 1H), 8.280 (s, 1H), 8.118 (s, 1H), 7.916 (s, 1H), 6.455 (s, 1H), 3.719 (s, 4H), 3.647 (s, 2H), 3.300 (s, 5H), 3.147 (s, 3H), 3.006 (s, 3H), 3.243 (t, 1H, J=7.6 Hz), 1.990-2.018 (m, 4H), 1.481 (s. 9H), 1.427 (s, 2H).

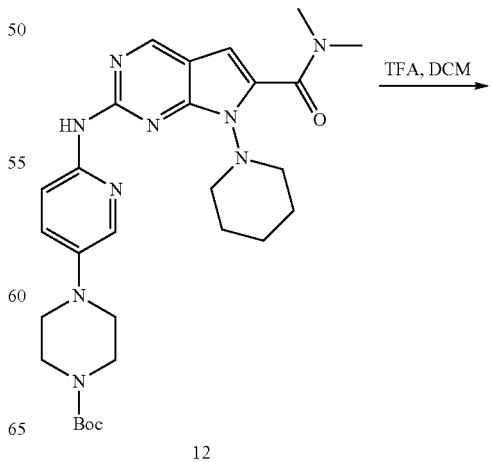

-continued

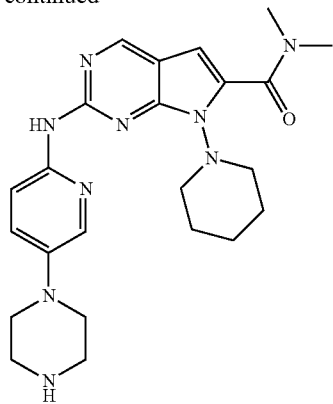

13

Compound 12 (68 mg, 0.1239 mmol) was dissolved in dichloromethane (10 mL), trifluoroacetic acid (2 mL) was added, and the reaction system was stirred at room temperature overnight. The reaction solution was evaporated to give a crud product which was purified by pre-TLC to give compound 13 as a yellow solid, yield: 59.34%. LCMS: 450 (M+H)+, RT=1.12 mim.

$^1$HNMR (MeOD, 400 MHz) δ (ppm) 8.680 (s, 1H), 8.308 (d, 1H, J=9.2 Hz), 7.972 (d, 1H, J=2.8 Hz), 7.498-7.528 (m, 1H), 6.413 (s, 1H), 3.990 (s, 2H), 3.344 (s, 1H), 3.138 (t, 6H, J=4.8 Hz), 3.056 (s, 3H), 2.987-3.011 (m, 4H), 2.121-2.205 (m, 1H), 1.986-2.088 (m, 1H)1.581-1.737 (m, 6H).

The following compounds can be obtained using similar methods:

N,N-dimethyl-2-((5-(4-methylpiperazin-1-yl)pyridin-2-yl)amino)-7-(piperidin-1-yl)-7H-pyrrolo[2,3-d]pyrimidine-6-carboxamide

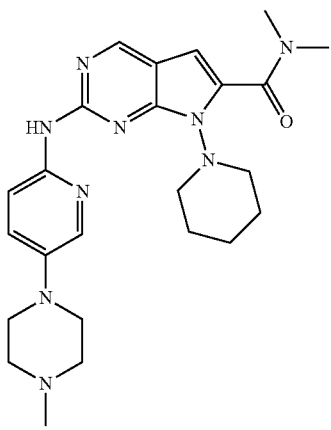

14

LCMS: 464 (M+H)+, RT=1.13 mim $^1$H NMR (DMSO, 400 MHz) δ (ppm) 9.361 (s, 1H), 8.732 (s, 1H), 8.240 (d, 1H, J=9.2 Hz), 8.006 (d, 1H, J=2.4 Hz), 7.465-7.493 (m, 1H), 6.379 (s, 1H), 3.857 (s, 2H), 3.132 (s, 5H), 3.020 (s, 3H), 2.952 (m, 3H), 2.479-2.490 (m, 4H), 2.234 (s, 3H), 1.196 (s, 1H), 1.547-1.703 (m, 6H).

7-(hexamethyleneimin-1-yl)N,N-dimethyl-2-((5-(piperazin-1-yl)pyridin-2-yl)amino)-7H-pyrrolo[2,3-d]pyrimidine-6-carboxamide

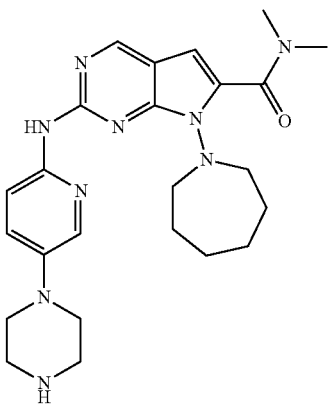

15

LCMS: 464 (M+H)+, RT=1.18 mim $^1$H NMR (MeOD, 400 MHz) δ (ppm) 8.686 (s, 1H), 8.373 (d, 1H, J=8.8 Hz), 8.006 (d, 1H, J=2.8 Hz), 7.565-7.595 (m, 1H), 6.397 (s, 1H), 5.338 (t, 1H, J=4.8 Hz), 3.958 (s, 2H), 3.221-3.245 (m, 4H), 3.158 (s, 3H), 3.065 (s, 3H), 2.156-2.209 (m, 1H), 2.002-2.048 (m, 2H), 1.781 (s, 6H), 1.581-1.674 (m, 4H).

Azetidin-1-yl-(2-((5-(4-methylpiperazin-1-yl)pyridin-2-yl)amino)-7-(piperidin-1-yl)-7H-pyrrolo[2,3-d]pyrimidin-6-yl)methanone

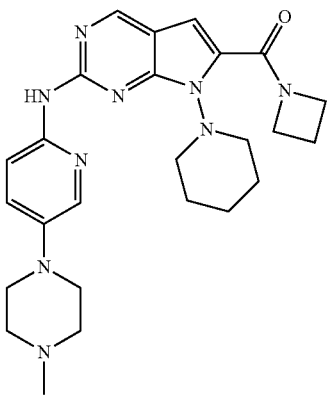

16

LCMS: 476 (M+H)+, RT=1.16 mim $^1$H NMR (MeOD, 400 MHz) δ (ppm) 8.696 (s, 1H), 8.316 (d, 1H, J=8.8 Hz), 7.985 (d, 1H, J=2.8 Hz), 7.514-7.544 (m, 1H), 6.593 (s, 1H), 4.288 (t, 2H, J=7.6 Hz), 4.208 (t, 2H, J=7.6 Hz), 3.953 (s, 2H), 3.232 (t, 4H, J=4.8 Hz), 2.710 (s, 4H), 2.367-2.424 (m, 4H), 2.152-2.187 (m, 1H), 2.019-2.033 (m, 1H), 1.787 (s, 5H), 1.598 (m, 1H).

43

Azetidin-1-yl-(2-((5-(piperazin-1-yl)pyridin-2-yl)amino)-7-(piperidin-1-yl)-7H-pyrrolo[2,3-d]pyrimidin-6-yl)methanone

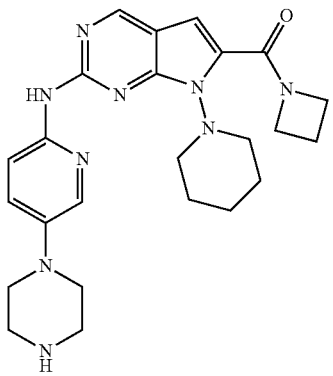

LCMS: 462 (M+H)+, RT=1.19 mim $^1$H NMR (MeOD, 400 MHz) δ (ppm) 8.706 (s, 1H), 8.351 (d, 1H, J=8.4 Hz), 8.008 (d, 1H, J=2.8 Hz), 7.543-7.573 (m, 1H), 6.602 (s, 1H), 4.290 (t, 2H, J=7.6 Hz), 4.210 (t, 2H, J=8 Hz), 3.952 (s, 2H), 3.215-3.229 (m, 6H), 2.349-2.427 (m, 2H), 2.152-2.205 (m, 2H), 2.008-2.033 (m, 1H), 1.788 (m, 1H), 1.787 (s, 5H), 1.598 (t, 1H, J=6.4 Hz).

N-methyl-2-((5-(piperazin-1-yl)pyridin-2-yl)amino)-7-(piperidin-1-yl)-7H-pyrrolo[2,3-d] pyrimidine-6-carboxamide

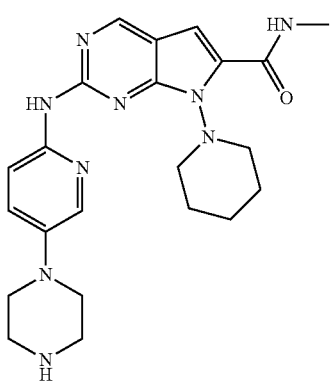

LCMS: 436 (M+H)+, RT=1.15 mim $^1$H NMR (MeOD, 400 MHz) δ (ppm) 8.777 (s, 1H), 8.7251 (d, 1H, J=9.2 Hz), 7.994 (d, 1H, J=2.8 Hz), 7.511-7.542 (m, 1H), 7.130 (s, 1H), 4.201 (t, 2H, J=10.8 Hz), 3.132-3.166 (m, 5H), 3.004 (s, 5H), 2.187 (t, 2H, J=7.6 Hz), 2.019-2.003 (m, 1H), 1.944 (s, 2H), 1.790 (d, 2H, J=13.6 Hz), 1.580-1.616 (m, 2H).

44

Tert-butyl 4-(6-(((6-(dimethylcarbamoyl)-7-(pyrrolidin-1-yl)-7H-pyrrolo[2,3-d]pyrimidin-2-yl)amino)pyridin-3-yl)piperazine-1-carboxylate

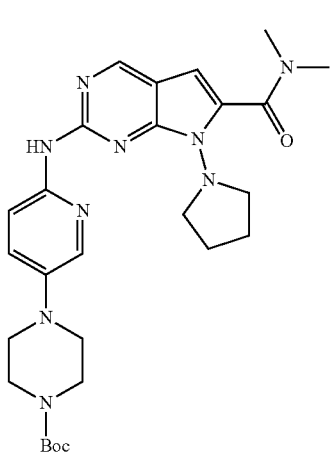

LCMS: 536 (M+H)+, RT=1.36 mim $^1$H NMR (CDCl3, 400 MHz) δ (ppm) 8.723 (s, 1H), 8.395 (d, 1H, J=9.2 Hz), 7.713 (d, 1H, J=9.2 Hz), 7.593 (s, 1H), 6.374 (s, 1H), 3.604 (d, 7H, J=13.6 Hz), 3.494 (s, 1H), 3.163 (s, 3H), 3.121 (s, 4H), 3.031 (s, 3H), 2.075 (s, 4H), 1.497 (s, 9H).

2-((5-(3,3-dimethylpiperazin-1-yl)pyridin-2-yl)amino)-N,N-dimethyl-7-(piperidin-1-yl)-7H-pyrrolo[2,3-d]pyrimidine-6-carboxamide

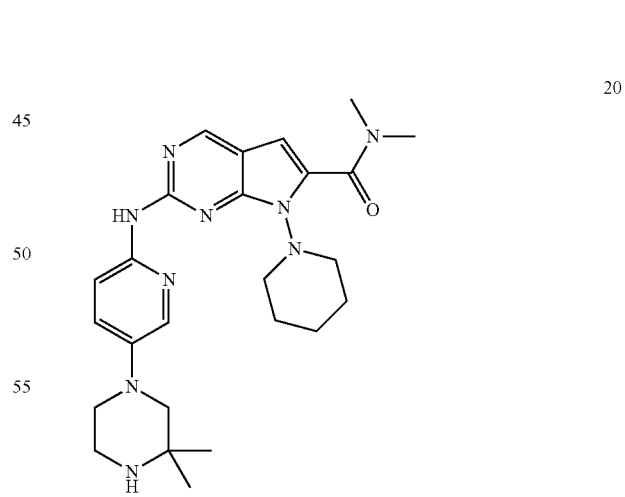

LCMS: 478 (M+H)+, RT=1.20 mim $^1$H NMR (MeOD, 400 MHz) δ (ppm) 8.720 (s, 1H), 8.277 (s, 1H), 8.018 (s, 1H), 7.624 (s, 1H), 6.434 (s, 1H), 4.003 (m, 2H), 3.477 (m, 1H), 3.141 (m, 4H), 3.049 (s, 3H), 2.177 (d, 2H, J=8 Hz), 2.026 (d, 4H, J=5.6 Hz), 1.735-1.757 (m, 3H), 1.580-1.616 (m, 3H), 1.471 (s, 4H), 1.401 (s, 2H).

45

(2-((5-(4-methylpiperazin-1-yl)pyridin-2-yl)amino)-7-(piperidin-1-yl)-7H-pyrrolo[2,3-d]pyrimidin-6-yl)-pyrrolidin-1-ylmethanone

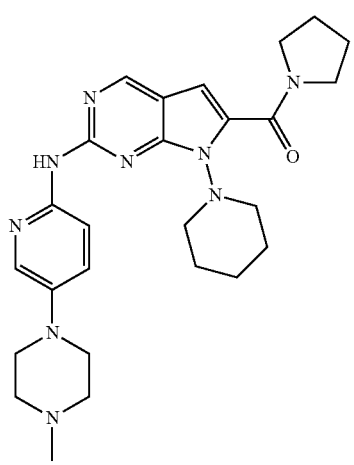

¹HNMR (400 MHz, DMSO-d6) δ9.37 (d, 1H, J=3.2 Hz), 8.72 (s, 1H), 8.24 (d, 1H, J=5.6 Hz), 8.00 (d, 1H, J=0.8 Hz), 7.48 (m, 1H), 6.45 (s, 1H), 3.45 (m, 4H), 3.15 (m, 6H), 2.28 (m, 4H), 1.96 (s, 3H), 1.84 (m, 6H), 1.64 (m, 8H).

N,N-dimethyl-2-((5-(4-methylpiperazin-1-yl)pyridin-2-yl)amino)-7-morpholino-7H-pyrrolo[2,3-d]pyrimidine-6-carboxamide

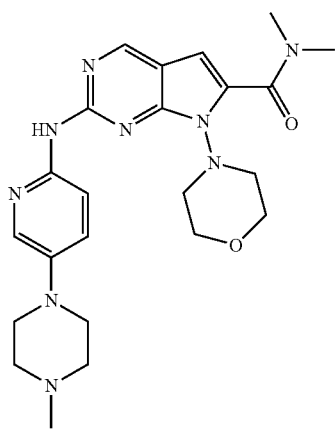

¹HNMR (400 MHz, DMSO-d6) δ9.36 (s, 1H), 8.74 (s, 1H), 8.16 (d, 1H, J=9.2 Hz), 8.00 (d, 1H, J=2.4 Hz), 7.39 (dd, 1H, J=2.8 Hz), 6.42 (s, 1H), 3.71 (m, 4H), 3.12 (t, 4H, J=4.6 Hz), 3.03 (s, 3H), 2.97 (s, 3H), 2.47 (m, 8H), 2.23 (s, 3H).

46

(2-((5-(piperazin-1-yl)pyridin-2-yl)amino)-7-(piperidin-1-yl)-7H-pyrrolo[2,3-d]pyrimidin-6-yl)-pyrrolidin-1-ylmethanone

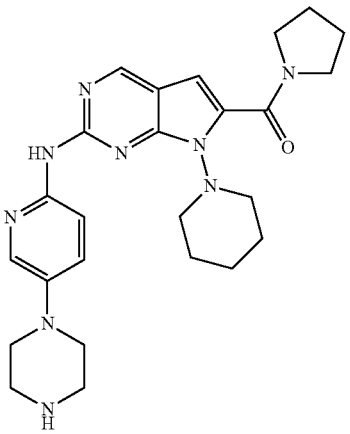

¹HNMR (400 MHz, DMSO-d6) δ9.38 (s, 1H), 8.73 (s, 1H), 8.23 (d, 1H, J=8.4 Hz), 8.00 (d, 1H, J=1.2 Hz), 7.46 (dd, 1H, J=6 Hz), 6.45 (s, 1H), 3.48 (m, 4H), 3.10 (m, 8H), 2.93 (m, 6H), 1.65 (m, 8H).

N,N-dimethyl-2-((5-(piperazin-1-yl)pyridin-2-yl)amino)-7-(pyrrolidin-1-yl)-7H-pyrrolo[2,3-d]pyrimidine-6-carboxamide

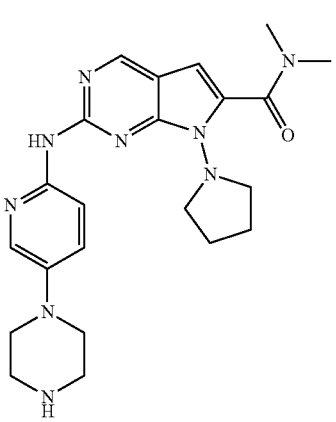

¹HNMR (400 MHz, MeOD-d4) δ8.69 (s, 1H), 8.20 (d, 1H, J=9.2 Hz), 7.97 (d, 1H, J=2.4 Hz), 7.52 (dd, 1H, J=2.8 Hz), 6.43 (s, 1H), 3.63 (m, 4H), 3.14 (m, 4H), 3.13 (s, 3H), 3.08 (s, 3H), 3.00 (m, 4H), 2.06 (m, 4H).

47

N,N-dimethyl-2-((5-morpholinopyridin-2-yl)amino)-7-(piperidin-1-yl)-7H-pyrrolo[2,3-d]pyrimidine-6-carboxamide

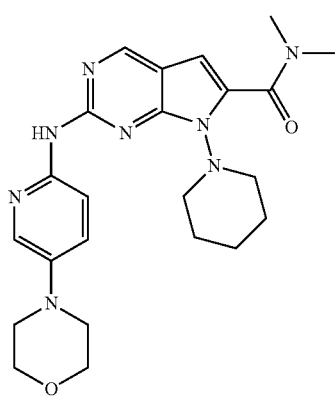

LCMS: 450 (M+H)+, RT=6.41 mim.

$^1$HNMR (CDCl3, 400 MHz) δ (ppm) 8.661 (s, 1H), 8.414 (d, 1H, J=8.8 Hz), 8.014 (d, 1H, J=2.4 Hz), 7.895 (s, 1H), 7.349-7.320 (m, 1H), 6.288 (s, 1H), 3.967-3.882 (m, 6H), 3.240-3.133 (m, 9H), 3.016 (s, 3H), 1.776-1.630 (m, 6H,).

N,N-dimethyl-2-((5-(4-ethylpiperazin-1-yl)pyridin-2-yl)amino)-7-(piperidin-1-yl)-7H-pyrrolo[2,3-d]pyrimidine-6-carboxamide

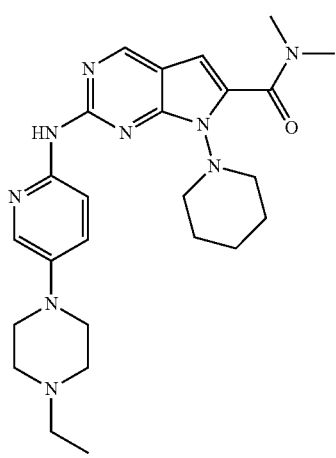

LCMS: 477 (M+H)+, RT=5.56 mim $^1$H NMR (DMSO-d6, 400 MHz) δ (ppm) 9.385 (s, 1H), 8.730 (s, 1H), 8.248 (d, 1H, J=8.8 Hz), 8.009 (S, 1H), 7.493 (d, 1H, J=8.4 Hz), 6.377 (S, 1H), 3.146 (S, 6H), 3.014-2.949 (m, 7H), 2.567 (m, 5H), 1.706-1.552 (m, 4H), 1.235 (s, 4H), 1.054 (s, 3H).

48

2-((5-((3S,5R)-3,5-dimethylpiperazin-1-yl)pyridin-2-yl)amino)-N,N-dimethyl-7-(piperidin-1-yl)-7H-pyrrolo[2,3-d]pyrimidine-6-carboxamide

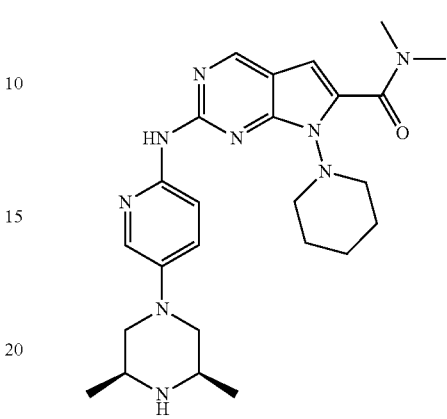

LCMS: 478 (M+H)+, RT=1.20 min.

$^1$HNMR (d6-DMSO, 400 MHz) δ (ppm) 9.30 (s, 1H), 8.72 (s, 1H), 8.22 (d, 1H, J=8.0 Hz), 7.97 (s, 1H), 7.46 (d, 1H, J=8.0 Hz), 6.37 (s, 1H), 3.83 (s, 1H), 3.49 (d, 2H, J=8.0 Hz), 3.01 (s, 3H), 2.94 (s, 3H), 2.89 (m, 2H), 2.33 (s, 1H), 2.14 (m, 2H), 2.01 (m, 2H), 1.23 (s, 6H), 1.04 (d, 6H, J=8.0 Hz), 0.85 (m, 1H).

N,N-dimethyl-2-((5-(piperazin-1-yl)pyridin-2-yl)amino)-7-morpholino-7H-pyrrolo[2,3-d]pyrimidine-6-carboxamide

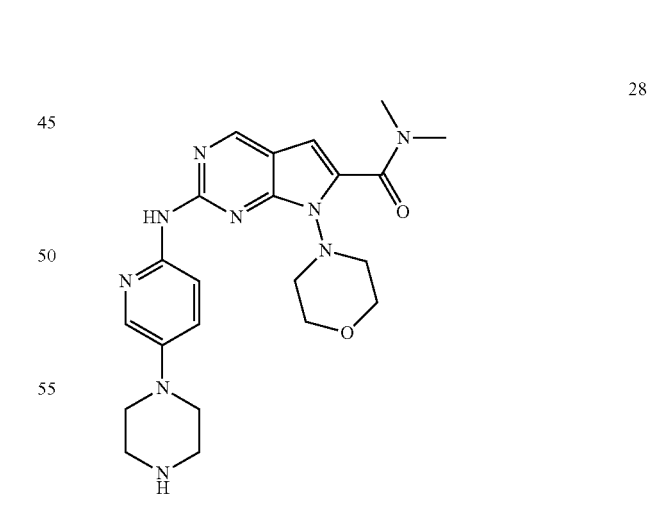

$^1$H NMR (400 MHz, DMSO-d6) δ9.47 (s, 1H), 8.77 (s, 1H), 8.17 (d, 1H, J=4 Hz), 8.01 (s, 1H), 7.40 (m, 1H), 6.43 (s, 1H), 3.71 (m, 8H), 3.03 (s, 6H), 3.00 (m, 4H), 2.87 (m, 4H).

49

N,N-diethyl-2-((5-(piperazin-1-yl)pyridin-2-yl)amino)-7-(piperidin-1-yl)-7H-pyrrolo[2,3-d]pyrimidine-6-carboxamide

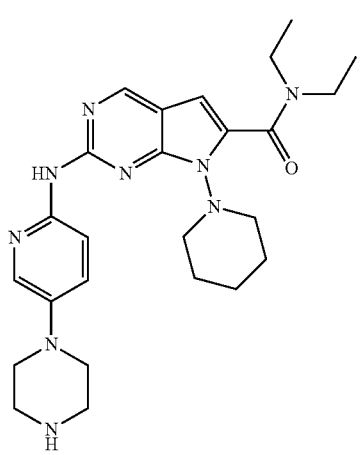

29

¹HNMR (400 MHz, MeOD-d4) δ8.72 (s, 1H), 8.35 (d, 1H, J=4 Hz), 8.02 (d, 1H, J=4 Hz), 7.55 (t, 1H, J=3 Hz), 6.42 (s, 1H), 4.01 (m, 2H), 3.61 (q, 2H, J=8 Hz), 3.39 (m, 4H), 3.17 (m, 4H), 3.03 (m, 4H), 1.83 (m, 4H), 1.64 (m, 4H), 1.34 (m, 8H).

N,N-dimethyl-2-((5-(4-deuteromethylpiperazin-1-yl)pyridin-2-yl)amino)-7-(piperidin-1-yl)-7H-pyrrolo[2,3-d]pyrimidine-6-carboxamide

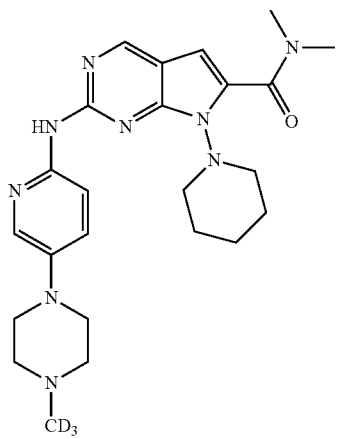

30

¹H NMR (DMSO-d6, 400 MHz) δ (ppm) 9.34 (s, 1H), 8.72 (s, 1H), 8.23 (d, J=9.2 Hz, 1H), 8.00 (s, 1H), 7.47 (dd, J=9.2 Hz, 1H), 6.37 (s, 1H), 3.51 (m, 2H), 3.21 (s, 6H), 3.01 (s, 3H), 2.95 (s, 3H), 1.68 (m, 10H).

50

N,N-dimethyl-2-((5-(4-methylpiperazin-1-yl)pyridin-2-yl)amino)-7-(homopiperidin-1-yl)-7H-pyrrolo[2,3-d]pyrimidine-6-carboxamide

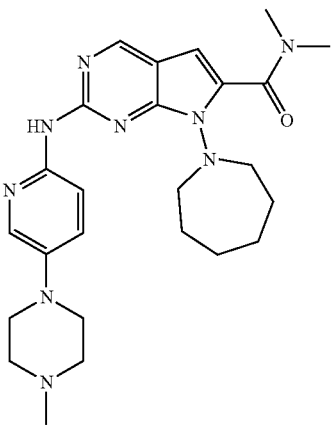

31

¹H NMR (DMSO-d6, 400 MHz) δ (ppm) 9.34 (s, 1H), 8.71 (s, 1H), 8.29 (d, J=9.2 Hz, 1H), 8.01 (s, 1H), 7.50 (m, 1H), 6.34 (s, 1H), 3.83 (m, 2H), 3.20 (m, 8H), 3.03 (s, 3H), 2.95 (s, 3H), 1.67 (m, 10H).

N,N-dimethyl-2-((5-(4-methyl-1,4-homopiperazin-1-yl)pyridin-2-yl)amino)-7-(piperidin-1-yl)-7H-pyrrolo[2,3-d]pyrimidine-6-carboxamide

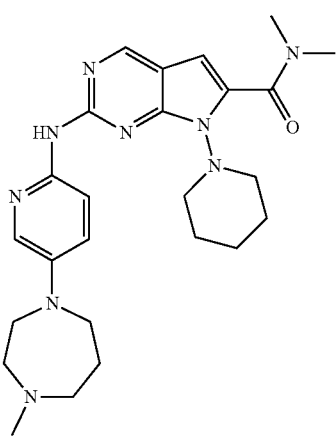

32

¹H NMR (DMSO-d6, 400 MHz) δ (ppm) 9.16 (s, 1H), 8.70 (s, 1H), 8.15 (d, J=8.0 Hz, 1H), 7.87 (d, J=2.8 Hz, 1H), 7.27 (m, 1H), 6.36 (s, 1H), 3.66 (s, 3H), 3.48 (m, 3H), 3.01 (m, 10H), 2.60 (s, 3H), 2.08 (s, 3H), 1.64 (m, 6H).

51

N,N-dimethyl-2-((5-((4-methylpiperazin-1-yl)methyl)pyridin-2-yl)amino)-7-(piperidin-1-yl)-7H-pyrrolo[2,3-d]pyrimidine-6-carboxamide

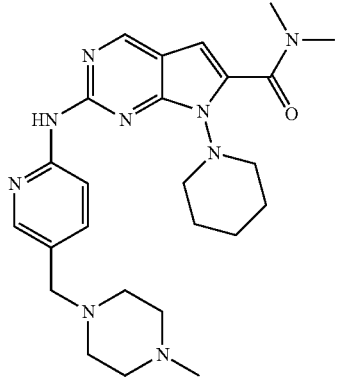

33

¹H NMR (methanol-d4, 400 MHz) δ (ppm) 8.98 (s, 1H), 8.31 (s, 1H), 8.20 (d, J=8.4 Hz, 1H), 7.53 (d, J=8.8 Hz, 1H), 6.64 (s, 1H), 3.98 (s, 2H), 3.71 (s, 2H), 3.57-3.43 (m, 2H), 3.34 (m, 2H), 3.16 (s, 6H), 3.06 (s, 4H), 2.91 (s, 3H), 2.52 (s, 2H), 1.76-1.60 (s, 6H).

N,N-dimethyl-2-((4-(4-methylpiperazin-1-yl)phenyl)amino)-7-(piperidin-1-yl)-7H-pyrrolo[2,3-d]pyrimidine-6-carboxamide

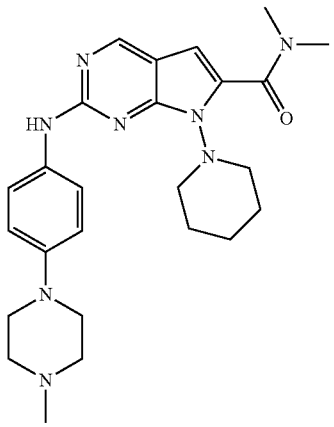

34

¹H NMR (DMSO-d6, 400 MHz) δ (ppm) 9.37 (s, 1H), 8.69 (s, 1H), 7.75 (d, J=8.0 Hz, 2H), 6.95 (d, J=8.4 Hz, 2H), 6.33 (s, 1H), 3.86 (m, 2H), 3.26-3.13 (m, 6H), 3.01 (s, 4H), 2.95 (s, 6H), 2.57 (s, 3H), 1.73-1.55 (m, 6H).

52

N,N-dimethyl-2-((5-(4-cyclopropylpiperazin-1-yl)pyridin-2-yl)amino)-7-(piperidin-1-yl)-7H-pyrrolo[2,3-d]pyrimidine-6-carboxamide

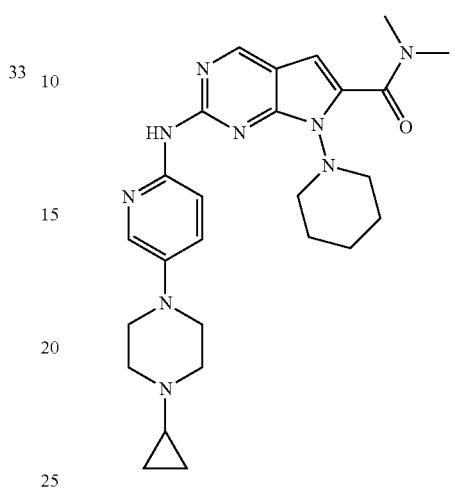

35

¹H NMR (DMSO-d6, 400 MHz) δ (ppm) 9.31 (s, 1H), 8.72 (s, 1H), 8.23 (d, J=8.8 Hz, 1H), 7.99 (d, J=2.8 Hz, 1H), 7.48 (m, 1H), 6.37 (s, 1H) 3.18 (d, J=5.6 Hz, 4H), 3.01 (s, 3H), 2.95 (s, 3H), 2.70 (t, J=8.8 Hz, 4H), 1.67 (m, 8H), 0.45 (d, J=4.4 Hz, 2H), 0.35 (d, J=2.8 Hz, 2H).

N,N-dimethyl-2-((6-(4-methylpiperazin-1-yl)pyridazin-3-yl)amino)-7-(piperidin-1-yl)-7H-pyrrolo[2,3-d]pyrimidine-6-carboxamide

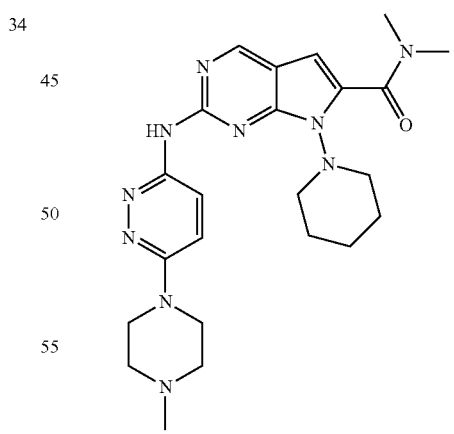

36

¹H NMR (DMSO-d6, 400 MHz) δ (ppm) 9.85 (s, 1H), 8.73 (s, 1H), 8.29 (d, 1H, J=10 Hz), 7.45 (d, 1H, J=9.6 Hz), 6.39 (s, 1H), 3.80-3.71 (m, 2H), 4.45 (s, 4H), 3.02 (s, 3H), 2.95 (s, 3H), 2.45 (s, 4H), 2.24 (s, 3H), 1.66-1.58 (m, 6H), 1.24 (s, 2H), 2-((5-(4-methylpiperazin-1-yl)pyridin-2-yl)amino)-7-(piperidin-1-yl)-7H-pyrrolo[2,3-d]pyrimidin-6-yl)methanol

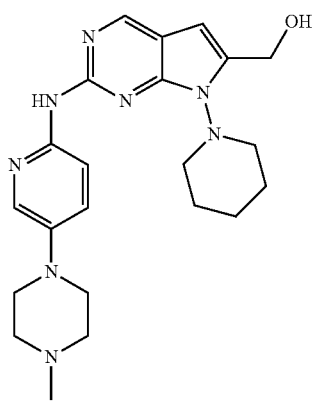

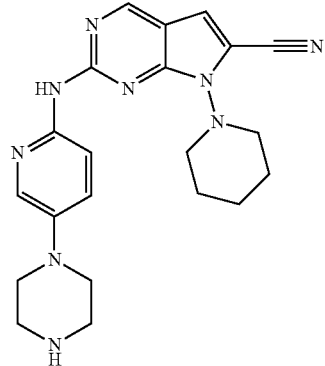

37

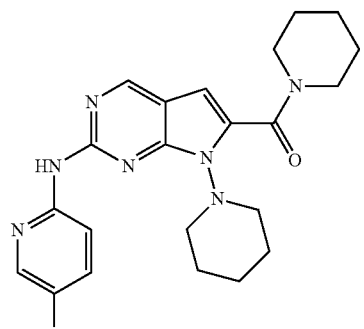

¹H NMR (DMSO-d6, 400 MHz) δ (ppm) 11.02 (s, 1H), 10.23 (s, 1H), 8.83 (s, 1H), 8.01 (s, 1H), 7.89 (d, 1H, J=8.4 Hz), 7.71 (d, 1H, J=8.8 Hz), 6.44 (s, 1H), 4.61 (s, 2H), 4.06-3.79 (m, 6H), 3.27-2.89 (m, 6H), 2.89 (s, 3H), 1.77-1.65 (m, 6H).

N,N-dimethyl-2-((5-(4-methylpiperazin-1-yl)pyridin-2-yl)amino)-5-methyl-7-(piperidin-1-yl)-7H-pyrrolo[2,3-d]pyrimidine-6-carboxamide

38

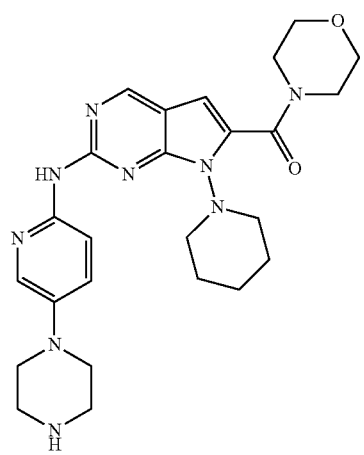

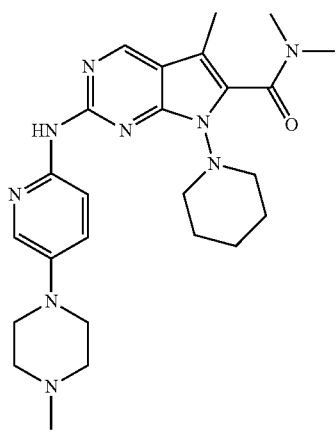

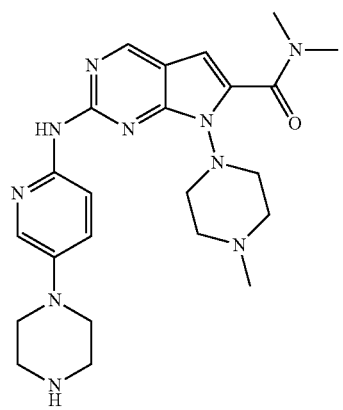

¹HNMR (CDCl₃, 400 MHz) δ (ppm) 8.58 (s, 1H), 7.93 (s, 2H), 7.37 (s, 1H), 3.98-3.93 (t, 3H, J=8.8 Hz, 10.8 Hz), 3.49 (s, 9H), 3.18-2.71 (m, 12H), 2.44 (s, 3H), 2.04-1.62 (m, 6H).

The following compounds can also be prepared in a similar manner:

-continued

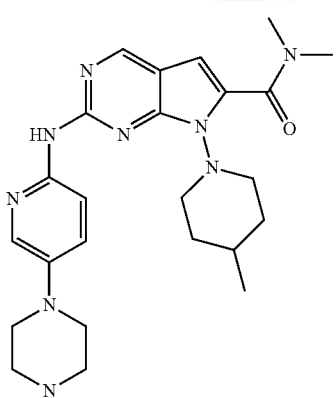
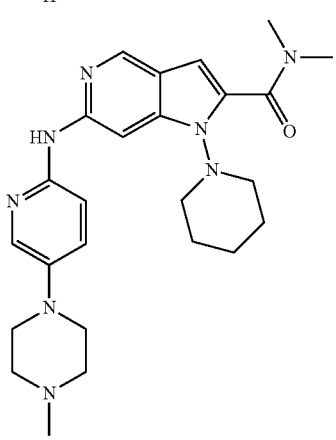
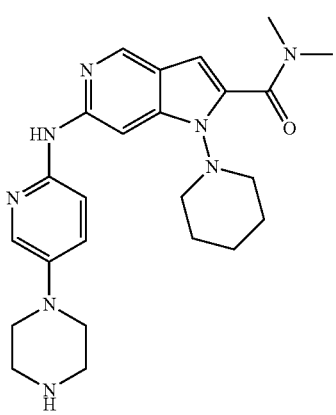
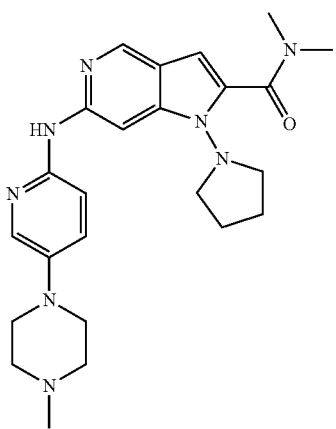

-continued

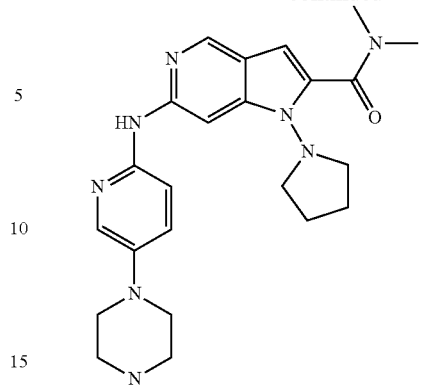
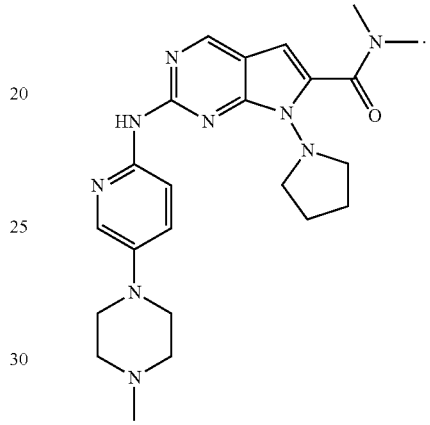

EXAMPLE 2

Determination of Activity of the Compounds of the Present Invention Against CDK Kinase 1. Experiment Material The CDK kinase used in this experiment: CDK4/CyclinD1 (invitrogen, Item No: PV4400); CDK6/CyclinD1 (invitrogen, Item No: PV4401); CDK1/CyclinB (invitrogen, Item No: PV3292).

Reagents used: Substrate is ULight-4E-BP1 (PerkinElmer, Item No: TRF0128); antibody is Eu-labeledantiphospho-eIF4E-bindingprotein1 (Thr37/46) (Perkin-Elmer, Item No: TRF0216).

2. Experimental Method

The test compound was dissolved in dimethyl sulfoxide and the solution was diluted to each concentration gradient with a buffer (50 mM HEPES, 10 mM MgCl$_2$, 1 mM EGTA, 2 mM DTT and 0.01% Tween20) according to the test needs, the concentration of dimethyl sulfoxide was 4%. The buffer was then used to dilute ATP and the substrate ULight-4E-BP1 to prepare the mixture of 800 μM ATP and 200 nM substrate for further use. 2.5 μL of mixture of substrate and ATP or 2.5 μL of substrate was added to the wells, and then 2.5 μL of compound or 4% buffer of dimethyl sulfoxide was added, finally 5 μL of enzyme (final concentration was 0.66 μg/mL) was added, incubated avoiding light at room temperature for 60 minutes. 5 μL of EDTA stop buffer (final concentration was 6 nM) diluted with 1×detectionbuffer (LANCEDetectionBuffer, 10×, PerkinElmer, CR97-100) was added to each well, and then 5 μL of antibody (final concentration was 2 nM) diluted with 1×detectionbuffer was added, incubated avoiding light at room temperature for 60 minutes. Perkin Elmer EnVision® TRFRETmode (Excitation wavelength: 320 nm, emission wavelength: 615 nm and 665 nm) was used to measure plates.

The inhibition rate of the sample was determined by the following formula:

$$\text{Inhibition rate (\%)} = \left(1 - \frac{\text{well signal ratio of compound-well signal ratio without } ATP \text{ control}}{\text{signal ratio of negative control-well signal ratio without } ATP \text{ control}}\right) \times 100\%$$

$IC_{50}$ values were calculated using GraphPadPrism software.

3. Results

The results are shown in Table 1. Symbol + represents $IC_{50}$ less than 100 nM, symbol ++ represents $IC_{50}$ as 100 nM to 500 nM, symbol +++ represents $IC_{50}$ greater than 500 nM, and symbol N/A represents no data.

TABLE 1

| Example number | CDK4 $IC_{50}$(nM) | CDK1 $IC_{50}$(nM) |
|---|---|---|
| 12 | + | N/A |
| 13 | + | +++ |
| 14 | + | +++ |
| 15 | + | +++ |
| 16 | + | +++ |
| 17 | + | +++ |
| 18 | + | +++ |
| 19 | + | N/A |
| 20 | + | +++ |
| 21 | + | +++ |
| 22 | ++ | N/A |
| 23 | + | +++ |
| 24 | + | +++ |
| 25 | + | +++ |
| 26 | + | +++ |
| 27 | + | +++ |
| 28 | ++ | N/A |
| 29 | + | +++ |

The results show that the compounds of the present invention can inhibit the activity of CDK4 kinase effectively at very low concentration (≤100 nM), and have a weak inhibitory activity against CDK1 kinase.

EXAMPLE 3

Determination of Proliferation Inhibitory Activity Against Human Colon Cancer Cell Line Colo205 for the Compounds of the Present Invention 1. Experimental Method In vitro cell assay described below could determine the proliferation inhibitory activity against human colon cancer cell line of the test compounds, and their activities could be represented by $IC_{50}$ value.

Colo205 cells (Chinese Academy of Sciences typical culture storage committee cell bank) were inoculated in 96-well culture plate with a suitable cell concentration of 2000 cells per hole, 140 μL of medium per well, then incubated in a carbon dioxide incubator at 37° C. overnight. 10 μL of different concentrations of the test compounds were added and reacted for 96 hours, and then the solvent control group (negative control) was set. The proliferation inhibitory activities against tumor cells of the test compounds were tested by CCK8 (CellCounting Kit-8, Item No: CK04, purchased from Tongren Chemical) method after 96 hours. The full-wavelength microplate reader SpectraMax190 was used for reading, the measurement wavelength was 450 nm.

The inhibition rate of the sample was determined by the following formula:

$$\text{Inhibition rate (\%)} = \left(1 - \frac{OD \text{ value of the compound well}}{OD \text{ value of negative control}}\right) \times 100\%$$

$IC_{50}$ value was calculated by four parameter regression using microplate reader with random software.

2. Results

The results are shown in Table 2. Symbol + represents $IC_{50}$ less than 0.5 μM, symbol ++ represents $IC_{50}$ as 0.5 μM to 2 μM, symbol +++ represents $IC_{50}$ greater than 2 μM, and symbol N/A represents no data.

TABLE 2

| Example number | Colo205 $IC_{50}$(μM) |
|---|---|
| 12 | +++ |
| 13 | ++ |
| 14 | ++ |
| 15 | +++ |
| 16 | ++ |
| 17 | +++ |
| 18 | ++ |
| 19 | +++ |
| 20 | ++ |
| 21 | +++ |
| 22 | N/A |
| 23 | +++ |
| 24 | +++ |
| 25 | +++ |
| 26 | ++ |
| 27 | ++ |
| 28 | N/A |
| 29 | +++ |

The results show that the compounds of the present invention can inhibit the proliferation of tumor cells effectively at low concentration (≤2 μM).

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A compound of formula I, or a pharmaceutically acceptable salt thereof:

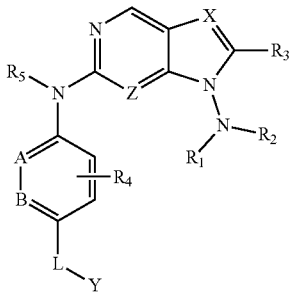

I wherein,

R₁ and R₂ can be connected with adjacent N atom to form a ring structure, said ring structure includes a substituted or unsubstituted 3-12 membered saturated or unsaturated heterocycle or a bridged ring or a spiro ring; wherein said heterocycle refers to a ring structure containing 0-3 heteroatoms selected from the group consisting of N, O or S, in addition to the nitrogen atom attached to the parent nucleus;

R₃ is selected from a substituted or unsubstituted C1-C8 alkyl, CN, C(O)OR₁₂, CONR₁₃R₁₄, C(O)R₁₅, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

R₄ is selected from H, a substituted or unsubstituted C1-C4 alkyl, a substituted or unsubstituted C1-C8 alkoxy, a halogen, OH, CN, C(O)OR₁₂, CONR₁₃R₁₄, C(O)R₁₅, a substituted or unsubstituted 5-8 membered aryl, a substituted or unsubstituted 5-8 membered heteroaryl, a substituted or unsubstituted 3-12 membered saturated or unsaturated heterocycle or carbocycle; wherein said heteroaryl contains 1-3 heteroatoms selected from the group consisting of N, O or S; said heterocycle contains 1-3 heteroatoms selected from the group consisting of N, O or S;

R₅ is selected from H or C1-C4 alkyl;

X is CR₁₆;

A and B are each independently selected from N or CR₁₆;

Z is N;

R₁₆ is H, C1-C4 alkyl or C1-C4 haloalkyl;

L is selected from the group consisting of none, C1-C6 alkylene, C(O), CONR₁₇ or S(O)₂;

Y is H, R₁₈, NR₁₉R₂₀, OH, or Y is selected from part of the group consisting of:

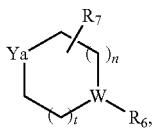

wherein,

R₆ is none, H, a substituted or unsubstituted C1-C8 alkyl, a substituted or unsubstituted C1-C8 alkoxy, a substituted or unsubstituted C2-C6 acyl, a substituted or unsubstituted C2-C6 sulfonyl, a substituted or unsubstituted C1-C6 alkylenehydroxy, CONR₂₂R₂₃ or C(O)R₂₄;

R₇ may be 0-3 substituents and R7 is a substituted or unsubstituted C1-C8 alkyl, an oxygen or a halogen, or two or more R₇ form a bridged cycloalkyl;

W is CR₂₁, N or O (when W is O, R₆ is absent);

Ya is CR₂₁ or N;

R₂₁ is H or a halogen;

R₈, R₉, R₁₀, R₁₁, R₁₂, R₁₃, R₁₄, R₁₅, R₁₇, R₁₈, R₁₉, R₂₀, R₂₂, R₂₃ and R₂₄ are each independently selected from H, a substituted or unsubstituted C1-C8 alkyl, a substituted or unsubstituted C1-C8 alkoxy, a substituted or unsubstituted C1-C6 alkyleneamino, a substituted or unsubstituted C1-C6 alkylenehydroxy, a substituted or unsubstituted 5-8 membered aryl, a substituted or unsubstituted 5-8 membered heteroaryl, a substituted or unsubstituted 3-12 membered saturated heterocycle or carbocycle; wherein said heteroaryl contains at least one heteroatom selected from the group consisting of N, O or S, said heterocycle contains at least one heteroatom selected from the group consisting of N, O or S;

n and t are 0, 1 or 2, respectively;

any one of the above mentioned "substituted" means that one or more hydrogen atoms on the group are substituted with substituent(s) selected from the group consisting of a halogen, OH, NH2, CN, an unsubstituted or halogenated C1-C8 alkyl, C1-C8 alkoxy, an unsubstituted or halogenated C2-C6 alkenyl, an unsubstituted or halogenated C2-C6 alkynyl, an unsubstituted or halogenated C2-C6 acyl, an unsubstituted or halogenated 5-8 membered aryl, an unsubstituted or halogenated 5-8 membered heteroaryl, an unsubstituted or halogenated 3-12 membered saturated heterocycle or carbocycle; wherein said heteroaryl contains 1-3 heteroatoms selected from the group consisting of N, O or S, said heterocycle contains 1-3 heteroatoms selected from the group consisting of N, O or S.

2. The compound of formula I of claim 1, wherein the compound of formula I is the compound selected from the group consisting of:

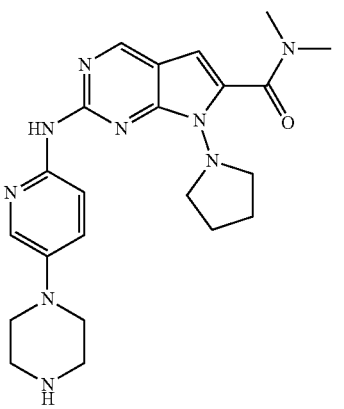

,

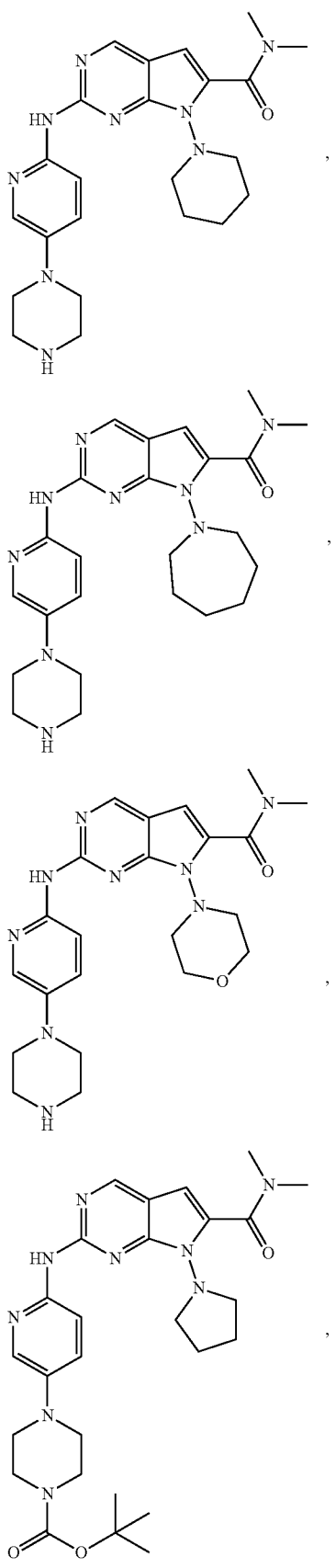
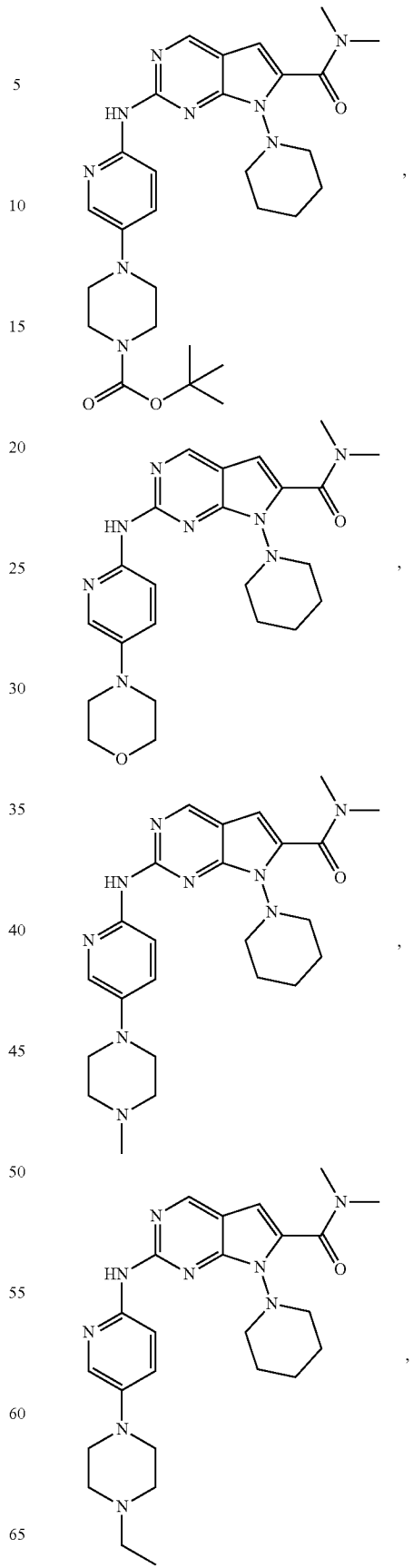

63
-continued
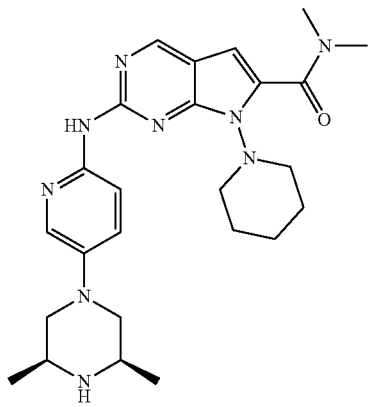
,
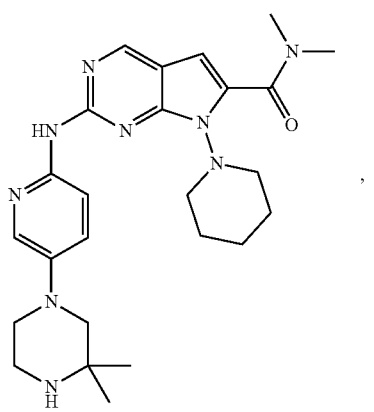
,
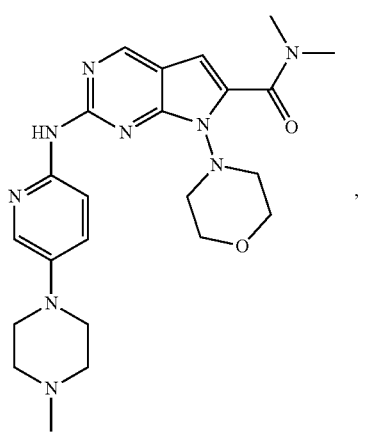
,
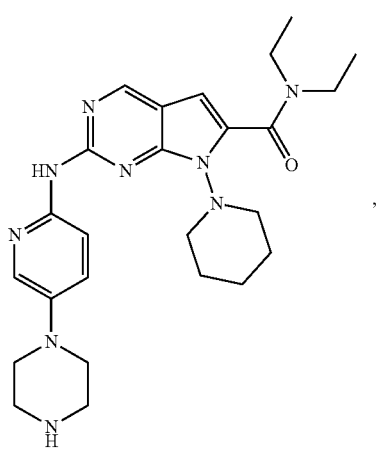
,
64
-continued
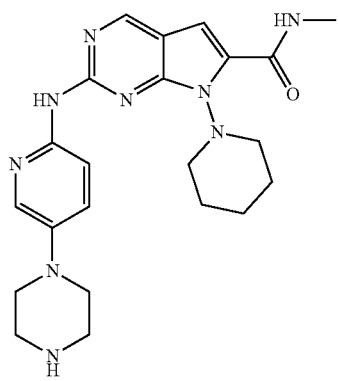
,
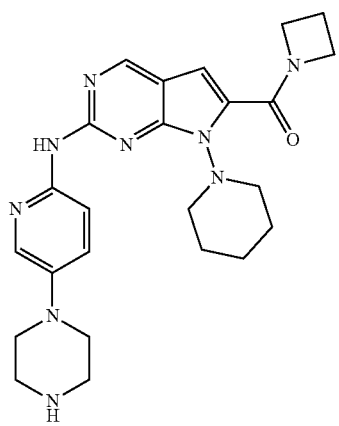
,
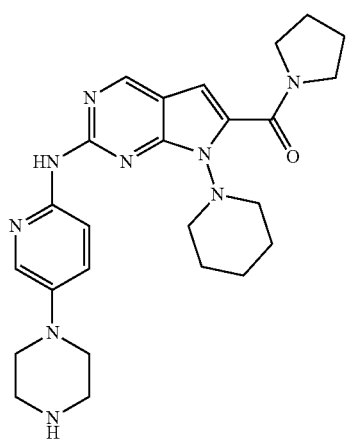
,
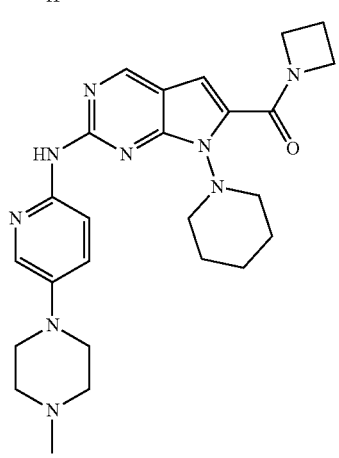
, 65
-continued
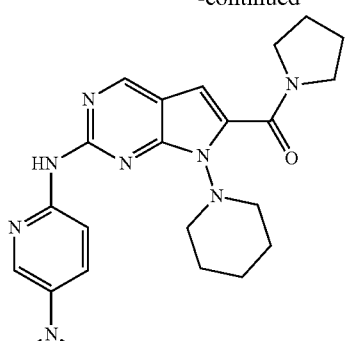
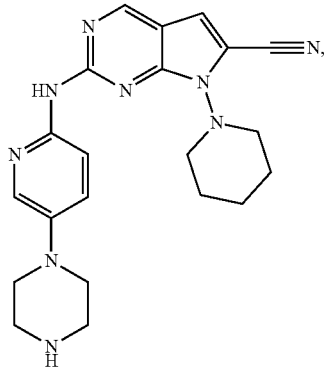
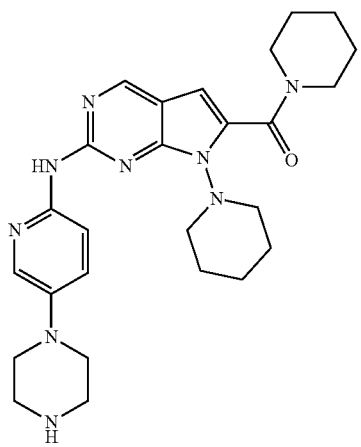
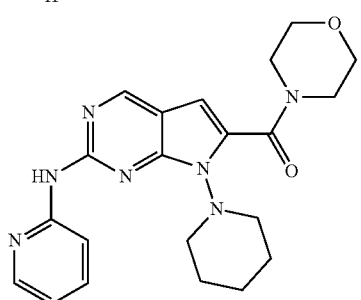
66
-continued
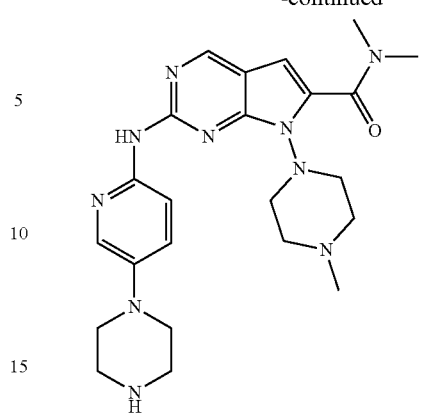
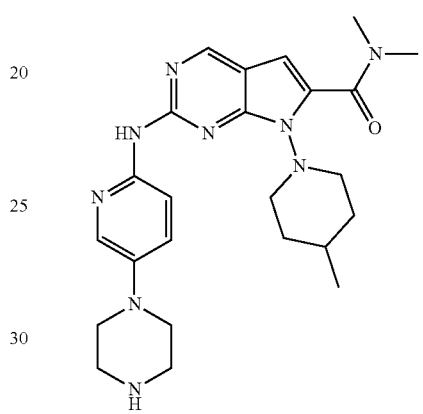
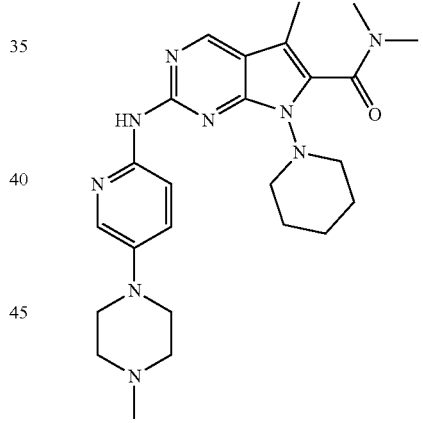
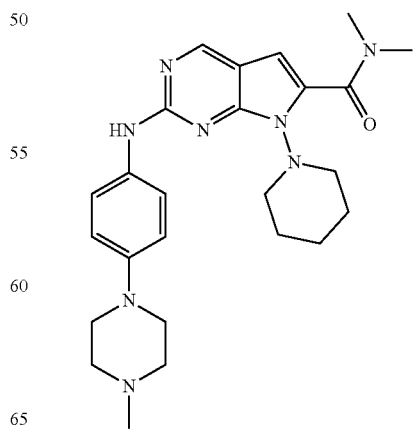

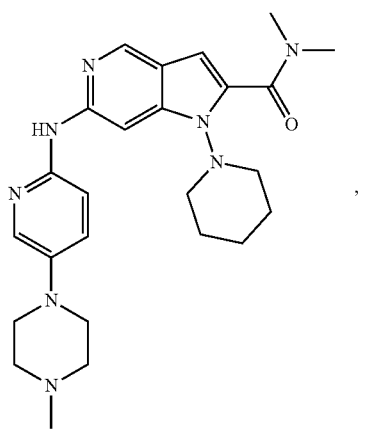
,
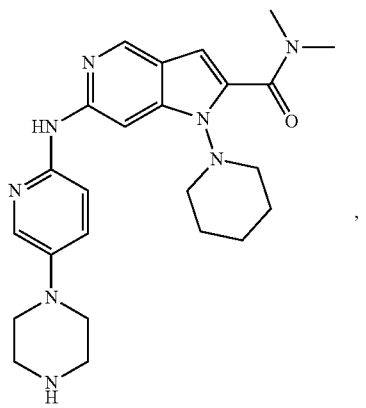
,
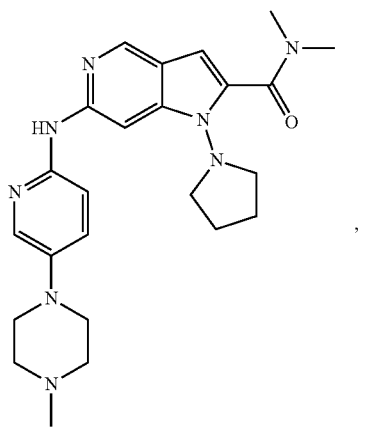
,
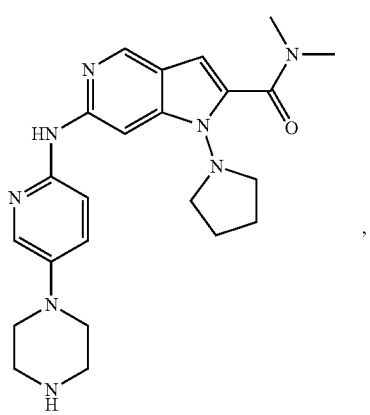
,
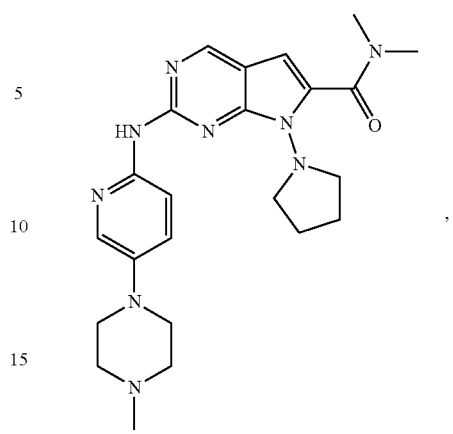
,
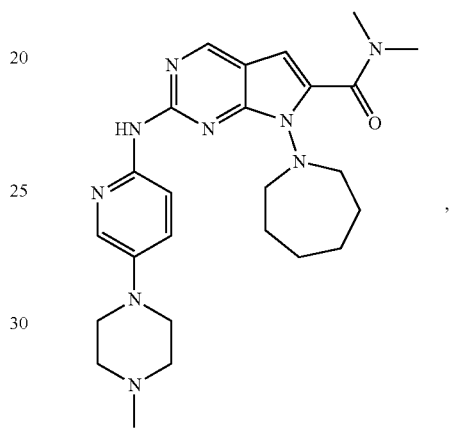
,
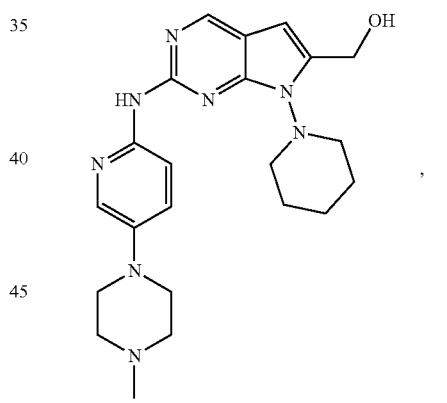
,
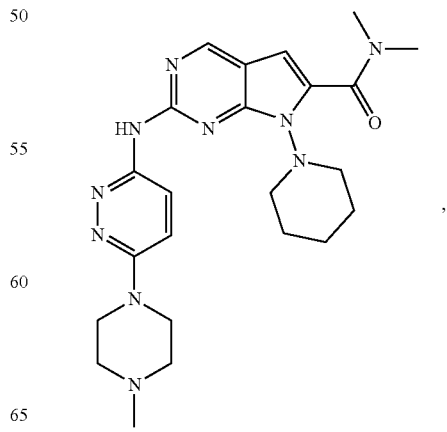
, -continued

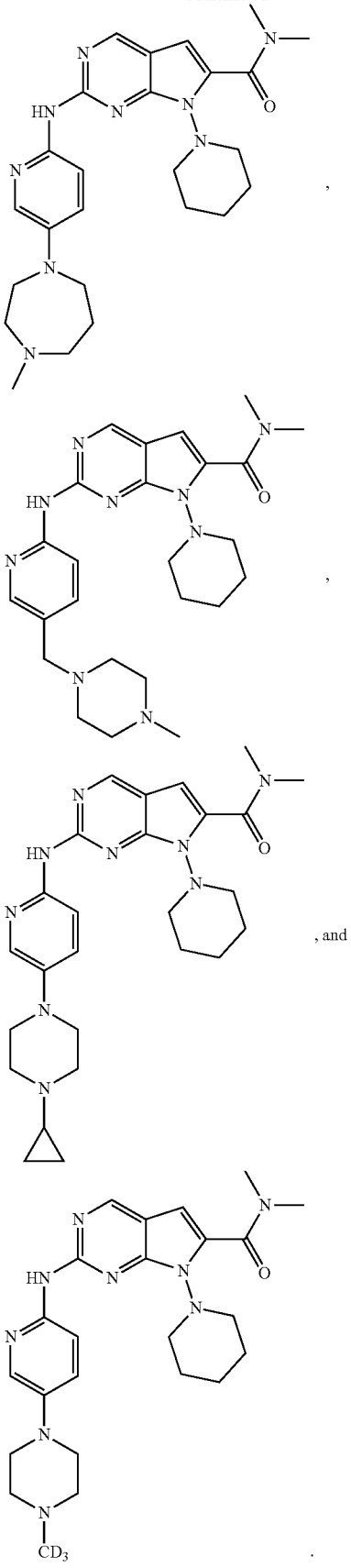

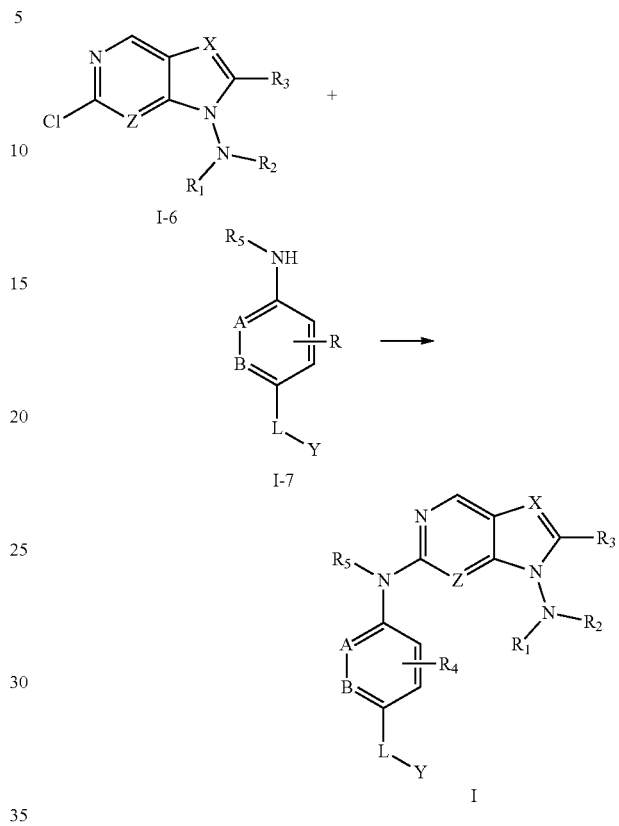

3. A process for the preparation of the compound of formula I of claim 1, wherein the process comprises the following step:

a) a compound of formula I-6 reacts with a compound of formula I-7 in an inert solvent to form the compound of formula I, wherein each group is defined as in claim 1.

4. The process of claim 3, wherein the inert solvent is selected from the group consisting of toluene, xylene, glycol dimethyl ether, dioxane, THF, DMF, DMSO, NMP, or a combination thereof.

5. The process of claim 3, wherein the process has one or more following characteristics:

the reaction is carried out in the presence of a palladium catalyst, and the palladium catalyst is selected from the group consisting of $Pd(PPh_3)_4$, $Pd_2(dba)_3$, $Pd(dba)_2$, $Pd(OAc)_2$, $Pd(PPh_3)_2Cl_2$, $Pd(dppe)Cl_2$, $Pd(dppf)Cl_2$, $Pd(dppf)Cl_2 \cdot CH_2Cl_2$, or a combination thereof;

the reaction is carried out in the presence of a ligand, and the ligand is a monodentate phosphine ligand or bidentate phosphine ligand; and the ligand is selected from the group consisting of triphenylphosphine, trimethylphenylphosphine, tricyclohexylphosphine, Tri-tert-butylphosphine, X-Phos, S-Phos, Binaphthyl diphenylphosphine, 1,1'-bis(diphenylphosphino)ferrocene, 1,2-bis(diphenylphosphino)ethane, Xant-Phos, or a combination thereof; and / or the reaction is carried out in the presence of a base, and the base is selected from the group consisting of $Na_2CO_3$, $K_2CO_3$, $Cs_2CO_3$, LiHMDS, NaHMDS, KHMDS, sodium tert-butoxide, potassium tert-butoxide, triethylamine, diisopropylamine, diisopropylethylamine, or a combination thereof.

6. A pharmaceutical composition, wherein the pharmaceutical composition comprises: (i) an effective amount of the compound of formula I set forth in claim 1, or a pharmaceutically acceptable salt thereof; and (ii) a pharmaceutically acceptable carrier.

7. A method of inhibiting CDK kinase activity, wherein the method comprises steps: administering a subject an inhibitory effective amount of the compound of formula I of claim 1, a pharmaceutically acceptable salt thereof, or a pharmaceutical composition comprising the compound of formula I or a pharmaceutical acceptable salt thereof.

8. A method of inhibiting tumor cells or treating cancer, wherein the method comprises: administering a subject an inhibitory effective amount of the compound of formula I of claim 1, a pharmaceutically acceptable salt thereof, or a pharmaceutical composition comprising the compound of formula I or the pharmaceutically acceptable salt thereof, wherein the cancer is selected from the group consisting of breast cancer, endometrial cancer, gastric cancer, bladder cancer, lymphoma, head and neck cancer, melanoma, non-small cell lung cancer, liver cancer, glioma, and colon cancer.

9. The method of claim 7, wherein the CDK kinase is CDK4, CDK6, or a combination thereof.

10. The method of claim 8, wherein the tumor cell is a leukemic cell line.

11. The method of claim 10, wherein the leukemic cell line is a myeloid leukemia cell line.

12. The method of claim 11, wherein the myeloid leukemia cell line is an acute myeloid leukemia cell line KG1.

13. The compound of formula I of claim 1, wherein A is N, and B is CH.

* * * * *